(12) United States Patent
Sato et al.

(10) Patent No.: US 7,630,537 B2
(45) Date of Patent: Dec. 8, 2009

(54) THREE-DIMENSIONAL SHAPE-MEASURING DEVICE

(75) Inventors: Isao Sato, Yokohama (JP); Hirooki Aoki, Yokohama (JP); Masato Nakajima, Yokohama (JP); Kazuhiro Mimura, Tokyo (JP); Yasuhiro Takemura, Tokyo (JP); Kei Katou, Tokyo (JP); Toshiharu Takesue, Tokyo (JP)

(73) Assignees: Sumitomo Osaka Cement Co., Ltd., Tokyo (JP); Keio University, Tokyo (JP)

( * ) Notice: Subject to any disclaimer, the term of this patent is extended or adjusted under 35 U.S.C. 154(b) by 499 days.

(21) Appl. No.: 10/560,048

(22) PCT Filed: Jun. 3, 2004

(86) PCT No.: PCT/JP2004/007717

§ 371 (c)(1),
(2), (4) Date: Jun. 5, 2006

(87) PCT Pub. No.: WO2004/109228

PCT Pub. Date: Dec. 16, 2004

(65) Prior Publication Data

US 2006/0239538 A1   Oct. 26, 2006

(30) Foreign Application Priority Data

Jun. 9, 2003    (JP) ............................. 2003-163503

(51) Int. Cl.
*G06K 9/00* (2006.01)

(52) U.S. Cl. .................... 382/154; 382/165; 250/574; 348/E5.029

(58) Field of Classification Search ................ 382/154, 382/254, 256, 257, 276, 282, 310, 283, 162, 382/165, 190, 181, 191; 209/580, 939; 356/71, 356/336, 335; 348/207.99, 254, 222.1, E5.024, 348/584, 586, 571, 578, 255, 126, E5.029, 348/E5.036, E5.041, E5.115, E5.037, 364; 205/574; 250/574
See application file for complete search history.

(56) References Cited

U.S. PATENT DOCUMENTS

| 4,882,566 A | 11/1989 | Koerber et al. |
| 4,947,152 A | 8/1990 | Hodges |
| 5,471,198 A | 11/1995 | Newham |

(Continued)

FOREIGN PATENT DOCUMENTS

CA    2 430 535 A1    6/2002

(Continued)

OTHER PUBLICATIONS

I. Sato et al., U.S. PTO Notice of Allowance, U.S. Appl. No. 10/560,027, dated Feb. 10, 2009, 6 pgs.

(Continued)

*Primary Examiner*—Sheela C Chawan
(74) *Attorney, Agent, or Firm*—Foley & Lardner LLP

(57) ABSTRACT

A 3-D shape measurement apparatus for grasping the state of an object with ease and accuracy is provided. The 3-D shape measurement apparatus includes: a first 3-D sensor 10a having a projecting device 11 for projecting a light pattern on a target area, and a (first) image capturing apparatus 12a placed at a first interval d1 from the projecting device 11 to capture an image of the target area on which the light pattern is projected; a second 3-D sensor 10b having a projecting device 11, and a (second) image capturing apparatus 12b placed at a second interval d2 longer than the first interval d1 from the projecting device 11 to capture an image of the target area on which the light pattern is projected; 3-D information computing means 22 for obtaining external shape information on an object 2 based on the shift of the pattern on the image acquired with the first 3-D sensor 10a; variation information computing means 23 for obtaining variation information on the object 2 based on the shift of the pattern on the image acquired with the second 3-D sensor 10b; and information composing means 24 for composing the external shape information and the variation information.

13 Claims, 14 Drawing Sheets

U.S. PATENT DOCUMENTS

| | | |
|---|---|---|
| 5,479,939 A | 1/1996 | Ogino |
| 5,528,339 A * | 6/1996 | Buhr et al. .................... 355/32 |
| 5,761,337 A * | 6/1998 | Nishimura et al. .......... 382/150 |
| 5,914,660 A | 6/1999 | Mesibov et al. |
| 6,011,477 A | 1/2000 | Teodorescu et al. |
| 6,011,595 A * | 1/2000 | Henderson et al. .......... 348/590 |
| 6,049,281 A | 4/2000 | Osterweil |
| 6,075,883 A * | 6/2000 | Stern et al. .................. 382/144 |
| 6,965,690 B2 * | 11/2005 | Matsumoto ................. 382/154 |
| 7,106,885 B2 | 9/2006 | Osterweil et al. |
| 7,110,596 B2 | 9/2006 | Brodsky et al. |
| 7,167,575 B1 | 1/2007 | Nichani et al. |
| 7,431,700 B2 | 10/2008 | Aoki et al. |
| 7,545,279 B2 | 6/2009 | Sato et al. |

FOREIGN PATENT DOCUMENTS

| | | |
|---|---|---|
| EP | 0 919 184 A1 | 6/1999 |
| EP | 1 350 466 A1 | 10/2003 |
| EP | 1 410 755 A1 | 4/2004 |
| JP | 2002-122416 A | 4/2002 |
| JP | 2002-131017 A | 5/2002 |
| JP | 2002-175582 A | 6/2002 |
| JP | 2003-32672 A | 1/2003 |
| JP | 3689720 B2 | 6/2005 |
| JP | 3922694 B2 | 3/2007 |
| JP | 3979238 B2 | 7/2007 |

OTHER PUBLICATIONS

I. Sato et al., U.S. PTO Office Action, U.S. Appl. No. 10/560,027, dated Jan. 14, 2008, 10 pgs.

I. Sato et al., U.S. PTO Office Action, U.S. Appl. No. 10/560,027, dated Jun. 2, 2008, 8 pgs.

* cited by examiner (a)

(b)

IMAGE OF BRIGHT LINE

THREE-DIMENSIONAL SHAPE-MEASURING DEVICE

TECHNICAL FIELD

The present invention relates to a 3-D shape measurement apparatus. More specifically, the present invention relates to a 3-D shape measurement apparatus capable of easily and accurately grasping the state of an object.

BACKGROUND ART

Movement detection sensors have so far been proposed as movement detection devices for detecting the movement of an object such as a person, in a space such as a bathroom. As a typical example, there has been a monitoring apparatus for monitoring the breath of a sleeping person on a bed by projecting a pattern onto the sleeping person on the bed, continuously taking an image of the projected pattern, and calculating the shift amount of the pattern from the image taken continuously (See Patent Document 1, for example).

Patent Document 1: JP-A-2002-175582 (pp 5-9 and FIGS. 1-13)

DISCLOSURE OF THE INVENTION

Problem to be Solved by the Invention

With the conventional device described above, however, it is hard to simultaneously grasp the states of various parts of the object, for example the shape and the state of motion (including small motion such as the breath of the object). Moreover, there are cases in which errors, though small, occur depending on the parts (the thorax, abdomen, etc.) on the object (in case the object is a person, for example).

Therefore, an object of the present invention is to provide a 3-D shape measurement apparatus that makes it possible to grasp the state of an object with ease and accuracy.

Means for Solving the Problem

To accomplish the object, a 3-D shape measurement apparatus 1 according to one aspect of the invention as shown for example in FIGS. 1 and 3 includes: a first 3-D sensor 10a having a projecting device 11 for projecting a light pattern on a target area, and an image capturing apparatus 12a placed at a first interval d1 from the projecting device 11 to capture an image of the target area on which the light pattern is projected; a second 3-D sensor 10b having a projecting device 11 for projecting a light pattern on the target area, and an image capturing apparatus 12b placed at a second interval d2 longer than the first interval d1 from the projecting device 11 to capture an image of the target area on which the light pattern is projected; 3-D information computing means 22 for obtaining external shape information on an object 2 present in the target area based on the shift of the pattern on the image acquired with the first 3-D sensor 10a; variation information computing means 23 for obtaining variation information on the object 2 based on the shift of the pattern on the image acquired with the second 3-D sensor 10b; and information composing means 24 for composing the external shape information and the variation information.

In such configuration, there are provided: the first 3-D sensor 10a having the projecting device 11 for projecting the light pattern on the target area, and the image capturing apparatus 12a placed at the first interval d1 from the projecting device 11 to capture an image of the target area on which the light pattern is projected; and the second 3-D sensor 10b having the projecting device 11 for projecting the light pattern on the target area, and an image capturing apparatus 12b placed at the second interval d2 longer than the first interval d1 from the projecting device 11 to capture an image of the target area on which the light pattern is projected. It is therefore possible to find out the shift of the pattern on the image with each of the 3-D sensors, for example. It is also possible with the 3-D information computing means 22 to obtain the external shape information on the object 2 based on the shift of the pattern on the image acquired with the first 3-D sensor 10a, and to obtain with the variation information computing means 23 the variation information on the object 2 based on the shift of the pattern on the image acquired with the second 3-D sensor 10b. Further, by composing the external shape information and the variation information using the information composing means 24, it is possible to provide the 3-D shape measurement apparatus capable of grasping the state of the object with ease and accuracy.

In the typical configuration, the projecting device 11 is used commonly in both the first 3-D sensor 10a and the second 3-D sensor 10b, and the first image capturing apparatus 12a and the second image capturing apparatus 12b separate from the first image capturing apparatus 12a are provided. However, alternatively the first image capturing apparatus 12a and the second image capturing apparatus 12b may be common and the first projecting device and the second projecting device, separate from the first one, may be provided.

In the 3-D shape measurement apparatus 1 according to another aspect of the invention it is preferred that the information composing means 24 corrects the variation information according to the external shape information. With the configuration in this way more accurate variation information can be obtained using such correction.

In the 3-D shape measurement apparatus 1 according to still another aspect of the invention, it is preferably characterized in that the information composing means 24 performs the composition so as to find out the movement of each point of the object 2.

The 3-D shape measurement apparatus according to still yet another aspect of the invention includes information output means 40 for displaying the composed results of the information composing means 24.

With the configuration in this way it is possible to easily grasp for example the movement of each point on the object 2 by displaying the composed results of the information composing means 24 using information output means 40.

In the 3-D shape measurement apparatus 1 according to further aspect of the invention, it is preferably characterized in that the light pattern projected from the projecting device 11 is an array of bright spots.

In the 3-D shape measurement apparatus 1 according to further aspect of the invention, it is preferably characterized in that the 3-D information computing means 22 performs interpolation for points that lack the external shape information.

Effects of the Invention

With the present invention as described above, it is possible to provide a 3-D shape measurement apparatus that can grasp the state of an object with ease and accuracy, since there are provided with a first three-dimensional sensor having a projecting device for projecting a light pattern on a target area, and an image capturing apparatus placed at a first interval from the projecting device to capture an image of the target area on which the light pattern is projected; a second three-dimensional sensor having a projecting device for projecting a light pattern on the target area, and an image capturing apparatus placed at a second interval longer than the first interval from the projecting device to capture an image of the target area on which the light pattern is projected; three-dimensional information computing means for obtaining external shape information on an object present in the target area based on the shift of the pattern on the image acquired with the first three-dimensional sensor; variation information computing means for obtaining variation information on the object based on the shift of the pattern on the image acquired with the second three-dimensional sensor; and information composing means for composing the external shape information and the variation information.

This application is based on the Patent Applications No. 2003-163503 filed on Jun. 9, 2003 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

BEST MODE FOR CARRYING OUT THE INVENTION

Description will be hereinafter made of an embodiment of the present invention with reference to the drawings. The same or corresponding components in the drawings are given the same reference numerals and symbols, and redundant description will not be repeated.

FIG. 1 is a schematic external view of a monitoring apparatus 1 or a 3-D shape measurement apparatus as a first embodiment of the present invention. The monitoring apparatus 1 is constituted to monitor a target area. The monitoring apparatus 1 includes a first FG sensor 10a as first 3-D sensor, having a projecting device 11 for projecting a light pattern to a target area, and a first image capturing apparatus 12a placed at a first interval from the projecting device 11 to capture an image of the target area on which the light pattern is projected. The monitoring apparatus 1 also includes a second FG sensor 10b as second 3-D sensor, having the projecting device 11 for projecting a light pattern on the target area, and a second image capturing apparatus 12b placed at a second interval longer than the first interval from the projecting device 11 to capture an image of the target area on which the light pattern is projected. The monitoring apparatus 1 further includes a computing device 20 for controlling the first FG sensor 10a and the second FG sensor 10b. That is to say, the monitoring apparatus 1 is configured by including the first FG sensor 10a, the second FG sensor 10b, and the computing device 20. In the following description, in case no discrimination is made between the first FG sensor 10a and the second FG sensor 10b and between the first image capturing apparatus 12a and the second image capturing apparatus 12b, they are respectively called simply as the FG sensor 10 and the image capturing apparatus 12. Moreover, in the first FG sensor 10a and the second FG sensor 10b, a common projecting device 11 is used.

Further, the FG sensor 10 has a measurement device 14 for measuring the shift of the pattern on the image captured with the image capturing apparatus 12. In this embodiment, in the first FG sensor 10a and the second FG sensor 10b, the common measurement device 14 is used. In other words, the measurement device 14 measures the shift of the patterns on the images captured respectively with the first image capturing apparatus 12a and the second image capturing apparatus 12b. The projecting device 11 and the image capturing apparatus 12 are electrically connected to and controlled with the measurement device 14. In this embodiment, the measurement device 14 is constituted to be integral with the computing device 20.

The object is present in the target area. In this embodiment, the target area is the surface of a bed 3. The object is typically one that breathes. That is to say, the object is a person or an animal. Specifically in this embodiment, the object is a person 2.

The figures show the person 2 lying on the bed 3. In other words, the light pattern is projected on the person 2. When no person 2 is present on the bed 3, the light pattern is projected directly onto the bed 3. Also, for example, bedclothes may be placed over the person 2. In that case, the light pattern is projected on the bedclothes.

The light pattern that the projecting device 11 projects is typically an array of bright spots. In other words, the light pattern projected is a plurality of bright spots. Here, the light pattern is a pattern 11a made up of a plurality of bright spots 11b arranged approximately in a square lattice shape, as will be described later with FIG. 2. As shown in the drawing, the projecting device 11 projects the pattern 11a onto the bed 3. The plurality of bright spots projected on the bed 3 respectively correspond to a plurality of measurement points on the bed 3. That is to say, the position of each bright spot is the position of each measurement point. A measurement point is defined as a point that permits to measure the movement and height of the person 2 in the direction of height, as will be described later. Here, the height is the height from the surface of the bed 3. Details of the above constitutions are explained below.

First, setting up the FG sensor 10 is described. The projecting device 11 and the image capturing apparatus 12 are located above the bed 3. As shown, the projecting device 11 and the first image capturing apparatus 12a are located above the approximate center of the bed 3. The second image capturing apparatus 12b is located approximately above the head of the person 2. The first image capturing apparatus 12a is located at a first interval d1 from the projecting device 11, and the second image capturing apparatus 12b at a second interval d2. Here, the projecting device 11, the first image capturing apparatus 12a, and the second image capturing apparatus 12b are placed on a straight line. That is, here, the baseline direction of the first FG sensor 10a and the baseline direction of the second FG sensor 10b are parallel to each other and moreover on the same straight line. Incidentally, the second interval d2 is for example about 2 to 20 times the first interval d1, preferably about 5 to 15 times. In this embodiment, 10 times is selected. For example, if the first interval d1 is 60 mm, then the second interval d2 is 600 mm. Here, the angle of view of each image capturing apparatus 12 is set to be capable of covering the approximately central part of the bed 3. The distance between the projecting device 11 and the image capturing apparatus 12 is called a baseline length. The baseline length is the distance in the baseline direction in triangulation between the projecting device 11 and the image capturing apparatus 12. While the description here assumes that the projecting device 11, the first image capturing apparatus 12a, and the second image capturing apparatus 12b are placed on the same straight line, the placement is not limited thereto. In case they are not on the same straight line, it can be coped with by correcting the way they appear at the time of performing composition, for example, as will be described later.

Here, the baseline length is explained. The FG sensor 10, as will be described later referring to FIG. 4, is to measure the shift of bright spots forming a pattern. For example, the greater the height of the object (here, the person 2) or its movement in the height direction, the greater becomes the shift amount of the bright spots. Therefore, according to the concept explained later with FIG. 4, if the shift amount of a bright spot is great, a phenomenon may occur in which the bright spot leaps another bright spot adjacent to the one to be compared therewith. Here, the bright spot is determined to have shifted from the adjacent bright spot, so that the shift amount of the bright spot measured ends up in a smaller value. Thus, the shift amount of the bright spot cannot be accurately measured. In case the baseline length is short (the first interval d1) as is the case of the first FG sensor 10a, while the shift amount of the bright spot is small and so the leap described above is less likely to occur, discrimination from noise is hard for small movement amount. Further, in case the baseline length is long (the second interval d2) as is the case of the second FG sensor 10b, for example even small movement amount of the object is reflected greatly on the shift amount of the bright spot. Therefore, while it is possible to measure small height or small movement in the height direction, in some cases the leap occurs in case for example a great movement occurs.

Therefore, it is preferable to set the baseline length shorter for measuring for example the shape of the person 2, and longer for measuring for example the breathing motion. In other words, it is preferable, like this embodiment, to measure the shape of the person 2 based on the pattern shift obtained with the first FG sensor 10a, and measure the movement of the person 2 based on the pattern shift obtained with the second FG sensor 10b.

Thus, it is recommended to place the projecting device 11 and the second image capturing apparatus 12b apart from each other by some large distance. Placing in this way results in a longer baseline length, so that changes can be sensitively measured.

In this case, the projecting device 11 is placed, as shown, with its optical axis (direction of casting laser beam L1) approximately parallel to the vertical direction of the top surface of the bed 3. By the way, while the projecting device 11 is placed with its optical axis approximately parallel to the vertical direction of the top surface of the bed 3 as described above, it may also be tilted to the vertical.

Also here, the first image capturing apparatus 12a is placed with its optical axis approximately parallel to the vertical direction of the top surface of the bed 3. That is, the optical axis of the first image capturing apparatus 12a is placed parallel to the optical axis of the projecting device 11. The second image capturing apparatus 12b is placed with its optical axis tilted relative to the vertical direction of the top surface of the bed 3. Placing in this way makes it easy to place for example the second image capturing apparatus 12b and the projecting device 11 apart by some large distance. In other words, it is easy to secure a longer second interval d2. Further in other words, it is easy to use a long baseline length in triangulation. It is also possible to place the projecting device 11, the first image capturing apparatus 12a, and the second image capturing apparatus 12b with their optical axes directed parallel to each other.

While the FG sensor 10 and the computing device 20 are shown separately, they may be made integral in one component. In this way, the monitoring apparatus 1 may be downsized.

The projecting device 11 suitable for the monitoring apparatus 1 is described referring to the schematic perspective view, FIG. 2. Here, a case is described in which the target area is a flat surface 102 and the laser beam L1, to be described later, is cast vertical to the flat surface 102. The projecting device 11 includes a light beam generation section 105 as light beam generation means for generating a coherent light beam, and a fiber grating 120 (hereinafter simply called the grating 120). The coherent light beam emitted from the light beam generation section 105 is typically an infrared laser beam. The light beam generation section 105 is constituted to generate a parallel beam. The light beam generation section 105 is comprised typically with a semiconductor laser and a collimator lens (not shown in the drawing) for generating a parallel beam or the laser beam L1. The laser beam L1 is almost circular in cross section. When referring to as a parallel beam here, it may be substantially parallel and includes approximately parallel light beam.

Here, the grating 120 is placed parallel to the flat surface 102 (at right angles to Z-axis). The laser beam L1 is incident in the Z-axis direction on the grating 120. Then, the laser beam L1 is focused within a plane of each of the individual optical fibers 121 having lens effect, expands as divergent waves. The divergent waves interfere with each other and the pattern 11a of an array of a plurality of bright spots is projected on the flat surface 102 as the projection surface. Here, placing the grating 120 parallel to the flat surface 102 means, for example, placing the plane including the axes of optical fibers 121 of FG elements 122 constituting the grating 120 parallel to the flat surface 102.

The grating 120 includes two FG elements 122 for constitution thereof. In this embodiment, the planes of respective FG elements 122 are parallel to each other. Hereinafter, the plane of each FG element 122 is called the element plane. In this embodiment, the axes of the optical fibers 121 of one FG element 122 are almost at right angles to those of the other FG element 122.

The FG element 122 is constituted for example with several tens to several hundreds of optical fibers 121 of several ten micrometers in diameter and about 10 mm in length, placed parallel in a sheet shape. The two FG elements 122 may be placed either in contact with each other or apart at an interval in the normal direction of the element plane. In the latter case, the interval between the two FG elements 122 is to the extent that does not affect the projection of the pattern 11a. The laser beam L1 is typically cast vertical to the element plane of the grating 122.

As described above, since in the projecting device 11 an optical system is the grating 120 including the two FG elements 122, no complicated optical system is required, so that the optical casing is made in a small size. Further, the projecting device 11 using the grating 120 makes it possible, in a simple structure, to project the pattern 11a of a plurality of bright spots 11b on the target area. Incidentally, the pattern 11a is typically made up of a plurality of bright spots 11b arranged in a square lattice shape. Further, the shape of the bright spot is nearly circular including elliptic.

Referring again to FIG. 1, the image capturing apparatus 12 is typically a CCD camera. The image capturing apparatus 12 has an imaging optical system 13a (See FIG. 4) and an image sensor 15 (See FIG. 4). The image sensor 15 is typically a CCD. In addition to CCD, elements of CMOS structure have been disclosed frequently of late as the image sensor 15. Therefore, they may be also used as a matter of course. In particular among them, there are those with element itself having the functions of frame-to-frame subtraction and binarization. Using such elements is preferable.

The image capturing apparatus 12 is preferably provided with a filter 13b (See FIG. 4) for dimming the light of wavelengths other than that around the wavelength of the laser beam L1 generated with the light beam generation section 105 described (See FIG. 2). The filter 13b is typically an optical filter such as an interference filter, preferably placed on the optical axis of the imaging optical system 13a. With this construction, the image capturing apparatus 12 can relatively increase the intensity of light of the pattern 11a projected by the projection device 11 out of the light received by the image sensor 15, and hence can reduce the influence of ambient light. The laser beam L1 emitted from the light beam generation section 105 is typically an infrared laser beam. The laser beam L1 may be cast either continuously or intermittently. In case of intermittent casting, image capturing with the image capturing apparatus 12 is to be synchronized with the timing of casting.

An exemplary constitution of the monitoring apparatus 1 is described in reference to FIG. 3, a block diagram. As described before, the computing device 20 is made integral with the measurement device 14. The measurement device 14 in turn is made integral with a control section 21 which will be described later. The projecting device 11 and the two image capturing apparatus 12 are electrically connected to and controlled with the measurement device 14. In this embodiment, the computing device 20 is remotely located relative to the projecting device 11 and the two image capturing apparatus 12. More specifically, it is placed for example by the side of the bed 3 or in a room different from the room the bed 3 is placed in, such as a nurse station or the like. The computing device 20 is typically a computer such as a personal computer.

First, the measurement device 14 is described. The measurement device 14 is to measure the shift of the pattern on the image captured with the image capturing apparatus 12. The measurement device 14 is constituted to obtain the image captured with the image capturing apparatus 12. The measurement device 14 is further constituted to measure the shift of each bright spot on the image captured with the image capturing apparatus 12. Incidentally, here for the convenience' sake, the projected bright spot and the bright spot image on the captured image are both called simply the bright spot. Here, measuring the bright spot shift means measuring the shift amount of the bright spot. Further, the shift amount of the bright spot measured is the concept including the direction of the bright spot shift. That is to say, the shift amount of the bright spot is to include information on the direction of shift.

Here, measurement of the bright spot shift using the measurement device 14 is described in detail. The measurement device 14 is constituted to measure the shift of the bright spot based on the images at two different time points captured respectively with the two image capturing apparatus 12. In this embodiment, the images at two different time points are further constituted to measure the shift of the bright spot based on the first images at the first two different time points and the second images at the second two different time points. Further, it is constituted that the first images at the first two different time points are acquired from the first image capturing apparatus 12a, and the second images at the second two different time points are acquired from the second image capturing apparatus 12b.

First, measurement of the bright spot shift based on the first images at the first two different time points is explained. The first two different time points are an arbitrary time point (the present time) and a time point at which the person 2 is not present on the bed 3. In the following description, an image captured at an arbitrary time point (the present time) is called the captured image, and the image captured at the time point at which the person 2 is not present on the bed 3 is called the base image. The base image is to be stored in a storage section 31.

Here, while the captured image and the base image are the images captured for example with the image capturing apparatus 12 (here, the first image capturing apparatus 12a), they also include information on the positions of the bright spot on respective images. In other words, the captured image and the base image are the images of the pattern 11a formed by projection with the projecting device 11 at respective time points. In this embodiment, the base image is stored in the storage section 31 for example not as the so-called image but in the form of position information such as coordinates related to the position of each bright spot. In this way, the process of measuring the bright spot shift amount described later becomes simple because only comparison of coordinates and directions of the bright spots suffices its purpose. Further, here, the position of the bright spot is set to the center of gravity of the bright spot. In this way, it is possible to measure even very small shift of the bright spot.

The bright spot shift amount is measured by comparing the information on each bright spot position on the base image stored in the storage section 31 with the information on each bright spot position on the captured image. Each shift amount can be obtained for example by counting the number of pixels by which the bright spot has shifted (distance for the number of pixels the bright spot has shifted). In this way the process is simplified because a differential image need not be produced as described later.

While the above description is made about the case of comparing information on the bright spot positions, it is also possible to create a differential image from the base image and the captured image. In that case, the bright spot shift amount is measured from corresponding bright spot positions on the differential image. In this way, only the bright spots that have shifted remain on the differential image, so that the amount of process is reduced.

Further, the bright spot shift amount measured with the measurement device 14 may be the shifting average or period average of the bright spot movement amount measured in the past for a certain number of times or a certain period of time. In this way, it is possible to reduce random noise or accidental noise caused by a flicker of incident sunlight through a window, so that reliability in the measured bright spot shift amount is improved.

The measurement device 14 is constituted as described above to measure the bright spot shift for each of the bright spots forming the pattern 11a. In other words, the plurality of bright spot positions are used as the plurality of measurement points. The measurement device 14 outputs the bright spot shift measured for each bright spot constituting the pattern 11a, or the measured bright spot shift, as a measured result, to the control section 21. In other words, the measured result is the bright spot shift amount measured based on the images at the first two different time points. Further, this measured result corresponds to the height of the person 2. Hereinafter the measured result is called the height information. The measurement device 14 outputs the measured result at each measurement point as a piece of height information.

Next, measuring the bright spot shift based on the second images at the second two different time points is described. This measurement is made like the above-described measurement of the bright spot shift based on the first images at the first two different time points. However, the second two different time points are set to an arbitrary time point and another time point slightly before the arbitrary time point. 'Slightly before' may be before by any time interval that is enough for detecting the movement of the person 2. The time interval may be chosen short when a slight movement of the person 2 is to be detected. An extent of time such as about 0.1 seconds may be chosen so that for example the movement of the person 2 does not become too great and the motion can be substantially deemed to be almost nonexistent. Or it may be chosen to be 1-10 TV periods (1/30-1/3 seconds). Further, in case general movement of the person 2 is to be detected, the interval may be chosen long, such as about 10 seconds. However, in case the breath movement of the person 2 is to be detected as in this embodiment, too long an interval makes accurate detection impossible. Therefore, choosing too long an interval such as one minute is inappropriate.

In the following description, an image captured (in the past) slightly before the captured image is assumed to be a reference image. That is, the second images at the second two different time points are the above-mentioned captured image and the reference image. The reference image, like the base image, is also taken with the image capturing apparatus 12 (here, the second image capturing apparatus 12b) including the concept of information on the bright spot position on each image. In this embodiment, the reference images are stored in the storage section 31 in the form of position information such as coordinates for each bright spot. The position of the bright spot is likewise assumed to be the center of gravity of the bright spot.

Further in this embodiment, the second images at the second two different time points are assumed to be an captured image (N-th frame) and an image ((N−1)th frame) captured before the captured image. In other words, the reference image is the image captured one frame before the captured image. The interval of capturing images may be appropriately chosen according to for example the processing speeds of devices and the manner of the movement to be detected; for example about 0.1 to 3 seconds, preferably 0.1 to 0.5 seconds. Capturing images at shorter intervals and processing them by averaging or filtering is advantageous because influence of for example random noise is reduced.

The waveform obtained by measuring the bright spot shift (for example the sum total of bright spot shift amounts) based on the images at two different time points, at an arbitrary time point and the time point slightly before it, becomes differential waveform of distance or a waveform representing changes in speed. In case a waveform representing changes in height is to be obtained, a waveform of distance or a waveform representing changes in height can be obtained by integrating the above waveform.

Further, the measurement device 14 is constituted to measure the bright spot shift amount including the direction of the bright spot shift, like the case of the first two different time points, by comparing the position information on each bright spot on the reference image stored in the storage section 31 with the position information on each bright spot on the captured image. Further likewise, the measurement device 14 outputs the bright spot shift amount measured for each bright spot as the measured result to the control section 21. In other words, the measured result is the bright spot shift amount measured based on the second images at the second two different time points. Further, the measured result, as described later with FIG. 4, corresponds to the movement in the height direction of each bright spot (measurement point) on the object, the person 2 in this case. Hereinafter the measured result is called the movement information. The measurement device 14 outputs the measured result at each measurement point as the movement information. The movement in the height direction of the person 2 is for example the movement occurring along with the breath of the person 2.

Here, the concept of bright spot shift is described referring to FIG. 4, a conceptual perspective view. Here, to make the description easy to understand, the target area is assumed to be a flat surface 102, and the object is assumed to be a solid 103. Further for the sake of description, the case is assumed in which the first images at the first two different time points are used as the base image and the captured image. Further, description is made on the assumption that the base image is the image of the pattern 11a when no solid 103 is present on the flat surface 102, and the captured image is the image of the pattern 11a when the solid 103 is present on the flat surface 102. Also for the sake of description, the case is assumed in which one image capturing apparatus 12 is used.

In the figure, the solid 103 is placed on the flat surface 102. An X-Y-Z orthogonal coordinate system is set with the X and Y axes on the flat surface 102. The solid 103 is placed in the first quadrant of the X-Y-Z coordinate system. The projecting device 11 and the image capturing apparatus 12 are placed above the flat surface 102 on the Z-axis. The image capturing apparatus 12 captures an image of the flat surface 102 on which the projecting device 11 projects the pattern 11a. In other words, an image of the solid 103 placed on the flat surface 102 is captured.

An imaging lens 13a, an imaging optical system of the image capturing apparatus 12 here, is arranged with its optical axis aligned with the Z-axis. The imaging lens 13a forms the image of the pattern 11a on the flat surface 102 or the solid 103 onto an image plane 15' (image plane) of the image sensor 15 of the image capturing apparatus 12. The image plane 15' is typically a plane intersecting the Z-axis at right angles. Further, an x-y coordinate system is assumed on the image plane 15' with the Z-axis passing the origin of the x-y coordinate system. The projecting device 11 is placed at a point apart from the flat surface 102 by the same distance as that between the flat surface 102 and the imaging lens 13a, and apart by a distance d (baseline length d) in the negative direction of the Y-axis from the imaging lens 13a. The pattern 11a of a plurality of bright spots 11b is projected onto the solid 103 and the flat surface 102. Incidentally, the y-axis direction is also the direction of the baseline for triangulation.

The pattern 11a projected by the projecting device 11 onto the flat surface 102 does not reach part thereof where the solid 103 is present. In case the solid 103 is present, the bright spot 11b, to be otherwise projected to a point 102a on the flat surface 102, is projected to a point 103a on the solid 103. As the bright spot 11b has shifted from the point 102a to the point 103a, and the imaging lens 13a is apart from the projecting device 11 by the distance d (baseline length d), the bright spot 11b, which would be otherwise imaged on the point 102a' (x, y), is imaged on a point 103a' (x, y+$\delta$). In other words, the position of the image of the bright spot 11b changes by a distance $\delta$ in the y-axis direction according to presence or absence of the solid 103.

Accordingly, as shown for example in FIG. 5, the bright spot imaged on the image plane 15' of the image sensor 15 shifts in the y-axis direction by the distance of $\delta$ by the presence of the solid 103 having a height.

In this way, the position of the point 103a on the solid 103 can be specified in three dimensions by measuring the shift amount δ of the bright spot. In other words, for example the height of the point 103a can be found out. In this way, it is possible to measure the distribution of heights, or the shape in three dimensions, on the solid 103 by measuring the difference between a position on the image plane 15' on which a point would be imaged if the solid 103 were not present and another position on the image plane 15' on which the point is actually imaged. Or, the coordinates in three dimensions of the solid 103 can be measured. Further, by reducing the pitch of the pattern 11a or the interval of the bright spots 11b to the extent that does not obscure the correlation of the bright spots 11b, it becomes possible to measure the distribution of heights on the solid 103 more in detail according to that extent.

On the basis of the concept as described above, the measurement device 14 can measure the height of the object by measuring the bright spot shift amount. In case the bright spot shift is measured according to the second images at the second two different time points as described above, namely in case the bright spot shift is measured according to the captured image and the reference image, it is to find out the change in the bright spot shift amount. Therefore, although for example the absolute height of the person 2 cannot be measured, changes in height of the object can be measured. Thus, the method is advantageous to measuring the movement in the height direction of the person 2. The above concept is applicable to both the first FG sensor 10a and the second FG sensor 10b.

The measurement device 14 is also constituted to correlate the pattern 11a on the image taken with the first image capturing apparatus 12a and the pattern 11a on the image taken with the second image capturing apparatus 12b. In this case, correlation is established for the bright spots 11b forming the pattern 11a. In this way, correlation can be established for the bright spot shift amount at each bright spot position, or at each measurement point position between the height information and the movement information. For example, correlation can be established by clarifying in advance the views of the target area or the surface of the bed 3 as seen from the two image capturing apparatus 12.

Establishing the above correlation is described by way of a concrete example in reference to FIGS. 6 and 7. In preparation, optical axes of the first image capturing apparatus 12a and the second image capturing apparatus 12b are aligned or adjusted. To put it more concretely, for example the optical axes are adjusted so that the fields of the respective image capturing apparatus 12 overlap as much as possible. The correlation is made according to the following process.

First, an image of the pattern is taken with the first image capturing apparatus 12a and 3-D coordinates of each bright spot of the patterns are calculated. Then, conversion of coordinates is carried out as shown in FIG. 6 according to the 3-D coordinates and the placement of the respective image capturing apparatus 12. In this case as shown, the 3-D coordinates of each bright spot are converted from a coordinate system $(X_1, Y_1, Z_1)$ to another coordinate system $(X_2, Y_2, Z_2)$. Further, an imaging lens 13a'' of the second image capturing apparatus 12b is set to be the origin of the coordinate system $(X_2, Y_2, Z_2)$. Also in this case, similarity is used to calculate the position on the image plane 15b, of the second image capturing apparatus 12b, on which an image of the pattern (bright spot) is captured (See FIG. 7).

At the time of the conversion, the coordinate system $(X_1, Y_1, Z_1)$ is assumed to be the 3-D coordinate system of the first image capturing apparatus 12a, and the coordinate system $(X_2, Y_2, Z_2)$ to be that of the second image capturing apparatus 12b. The imaging lens 13a'' of the second image capturing apparatus 12b is set to be the origin of the coordinate system $(X_2, Y_2, Z_2)$. The distance between the first image capturing apparatus 12a and the second image capturing apparatus 12b is assumed to be dx. Further in consideration of optical layout, following equations are used to convert the coordinate system.

[Equation 1]

$$\begin{pmatrix} X_2 \\ Y_2 \\ Z_2 \end{pmatrix} = \begin{pmatrix} \cos\theta & 0 & -\sin\theta \\ 0 & 1 & 0 \\ \sin\theta & 0 & \cos\theta \end{pmatrix} \begin{pmatrix} X_1 - d_X \\ Y_1 \\ h - Z_1 \end{pmatrix} \quad (1)$$

The angle θ formed between the optical axis of the second image capturing apparatus 12b and the bed surface is determined with the equation below.

$$\theta = \text{arc tangent}(dx/h) \quad (2)$$

Next, another image of the pattern is taken with the second image capturing apparatus 12b. The position calculated as described before is compared with the pattern image taken with the second image capturing apparatus 12b. A bright spot in the nearest position is deemed to be the same bright spot and correlated.

While the above correlation process is made to all the bright spots on the image, in some cases the correlation cannot be made to some bright spots due to difference in the image field between the first image capturing apparatus 12a and the second image capturing apparatus 12b. Such bright spots are regarded as missing spots and not used for measurements.

Referring again to FIG. 3, the computing device 20 is described. The computing device 20 has the control section 21 for controlling the monitoring apparatus 1. The control section 21 in turn is connected to the storage section 31. The storage section 31 is preferably made to store in time sequence the images obtained from the image capturing apparatus 12. The storage section 31 can store data such as calculated information.

The control section 21 is connected to a display 40 as information output means for displaying the composed results from output information composing means 24 as information composing means which will be described later. The display 40 is typically an LCD. The display 40 receives and displays for example analyzed information outputted from the output information generating means 24. In case the information need not be outputted at the moment (in case for example simply storing the composed results), the display 40 need not be provided.

The control section 21 is also connected to an input device 35 for entering information for operating the monitoring apparatus 1. The input device 35 is for example a touch panel, keyboard, or a mouse. While the input device 35 is shown in the drawing as the one that is added from outside to the computing device 20, it may be built in the computing device 20. While this embodiment is described as being provided with the input device 35, it may not be provided.

Further, there are provided within the control section 21: a 3-D shape generation section 22 as 3-D information computing means for obtaining external shape information of the person 2 present on the bed 3 based on the shift of the pattern on the image acquired with the first FG sensor 10a; a variation information computing section 23 as variation information computing means for obtaining variation information on the person 2 based on the shift of the pattern on the image acquired by the second FG sensor 10b; and an output information generation section 24 as output information composing means for composing together the external shape information and the variation information. The external shape information and the variation information are explained below. The above constitution is described below in detail:

The 3-D shape generation section 22, as described above, is to obtain the external shape information on the person 2 present on the bed 3. In this embodiment, the external shape information is an image showing a 3-D shape (hereinafter simply called the 3-D shape). The 3-D shape generation section 22 generates a 3-D shape as external shape information based on the measured results, that is, the height information from the measurement device 14 of the first FG sensor 10a.

Generating the 3-D shape with the 3-D shape generation section 22 is described here. The 3-D shape generation section 22 is constituted to generate a 3-D shape based on the measured results or height information from the measurement device 14.

As described above, the height information or the measured results of the measurement device 14 corresponds to the height of the person 2 at a plurality of measurement points. In this case, the height is actually calculated from the height information. In this case, the height of the person 2 at each measurement point is calculated by triangulation based on the bright spot shift amount at each measurement point, or the height information. In additional words, height above the bed 3 is calculated. Calculating the height of the person 2 is explained in reference to FIG. 8. Here, to make the description easy to understand like the case of FIG. 4, the target area is assumed to be the flat surface 102, and the object is assumed to be the solid 103.

FIG. 8 is a line drawing as seen in the X-axis direction (See FIG. 4) to show the relationship between the projecting device 11, the image capturing apparatus 12, the solid 103, and the flat surface 102. In the description here, the height of the solid 103 is assumed to be Z1. The center of the projecting device 11 (center of the light pattern) and the center of the imaging lens 13a are apart by a distance of d parallel to the flat surface 102. The distance between the imaging lens 13a and the image plane 15' (image sensor 15) is 1 (about the same as the focal distance of the imaging lens 13a). The distance between the imaging lens 13a and the flat surface 102 is h. The height of the solid 103 from the flat surface 102 is Z1. It is assumed that the point 102a' on the image plane 15' is shifted by a distance of δ to a point 103a' as a result of the solid 103 being placed on the flat surface 102.

Assuming the point to be 102a", where the line interconnecting the center of the imaging lens 13a and the point 103a intersects the flat surface 102, and taking note of a triangle 103a'-102a'-13a and a triangle 102a"-102a-13a, the distance D between the points 102a and 102a" is D=δ·h/l. Taking note of a triangle 13a-11-103a and the 102a"-102a-103a, the distance D=(d·Z1)/(h−Z1). From these equations, Z1 is determined as follows:

$$Z1 = (h^2 \cdot \delta)/(d \cdot l + h \cdot \delta) \tag{3}$$

As described above, the height of the solid 113 can be calculated.

The 3-D shape generation section 22 is further constituted to make interpolation for points that lack the external shape information, that is, 3-D information. Incidentally, in case external shape information that is necessary is obtained enough, interpolation is not required.

Interpolation is explained here. As described above, the 3-D shape generation section 22 calculates the height of each measurement point from the height information which is the measured result of the measurement device 14, and generates a 3-D shape based on the calculated height. As for the height of the person 2, since respective measurement points (bright spots) are placed at intervals, the height of any point between two measurement points is unknown. Therefore, if a 3-D shape is generated directly from the heights of the person 2 at respective measurement points, the external shape of the person 2 is not easy to understand. To make up for this, the 3-D shape generation section 22 carries out interpolation for additional points with which the external shape can be understood easily.

To put it more specifically, four measurement points are searched that are located in the vicinity of a point defined with a set of 3-D coordinates (X, Y, Z) to be interpolated.

Assuming the 3-D coordinates of the four measurement points to be $(x_i, y_i, z_i)$, a distance is calculated from the following equation:

$$\delta i = \{(X-xi)^2 + (Y-yi)^2\}^{1/2} \tag{4}$$

and $$SUM\_A = \Sigma \delta_i \tag{5}$$

The height of (X, Y) is calculated using the equation (6) below:

[Equation 2]

$$Z = \sum_{i=1}^{4} \frac{(SUM\_A - \delta_i) z_i}{3 \cdot SUM\_A} \tag{6}$$

where, $z_i$ represents height at each measurement point.

The height of the person 2 at each coordinate between the measurement points can be interpolated by carrying out the above calculation for the sets of coordinates to be interpolated. The 3-D shape generation section 22 generates a 3-D shape by the interpolation as described above.

FIG. 9 shows an example of the 3-D shape generated as described above. Incidentally, the 3-D shape shown is the image when it is displayed on the display 40.

The interpolation is not limited to the above example but various interpolation methods or grid methods may be applied. (Such methods include: Triangulation; Radial Basis Function Interpolation; Polynomial Regression; Nearest Neighbor Grid Method; Natural Neighbor Grid Method; Modified Shepard's Method; Minimum curvature; Inverse Distance to a Power Grid Method; Kriging; and others.)

The variation information computing section 23 is to obtain variation information on the person 2 as described above. In this embodiment, the variation information is information related to movement in the height of the person 2 including phase of movement in the height direction of the person 2 at each measurement point. The variation information here is also assumed to include height variation amount which will be described later.

The variation information computing section 23 is constituted to recognize the phase of movement of each measurement point from the movement information, the results measured with the measurement device 14. The variation information computing section 23 obtains the phase of movement recognized at each measuring point as the variation information. In this case, the phase is a concept including the direction of movement. Further in this case, recognition of the phase of movement with the variation information computing section 23 is to recognize whether the movement measured at each measurement point with the measurement device 14 is directed upward or downward. In this way, it is possible for example to find out which point on the body of the person 2 is making upward or downward movement.

The variation information computing section 23 is also constituted to calculate the amount of change in height (hereinafter called the height change amount) of the person 2 at each measurement point as variation information according to the movement information. The variation information computing section 23 calculates height change amount based on the movement information, the results measured with the measurement device 14 of the second FG sensor 10b.

Here, calculating the height change amount with the variation information computing section 23 is described. The variation information computing section 23 is constituted to calculate the height change amount based on the movement information. As described before, while the movement information corresponds to the movement in height direction of the person 2 at each measurement point, in this case, actual height change amount is calculated from the movement information. In this case, like the height calculation described with FIG. 8 before, the height change amount of the person 2 at each measurement point is calculated by triangulation based on the bright spot shift amount of the movement information. It is also possible to carry out interpolation for the height change amounts like for the 3-D shape.

Next, the output information generation section 24 is described. The output information generation section 24 is to compose the 3-D shape and the variation information. The output information generation section 24 is constituted to generate analysis information to be displayed by composing the 3-D shape obtained with the 3-D shape generation section 22 and the variation information obtained with the variation information computing section 23. The analysis information generated is outputted to and displayed on the display 40. Incidentally, the term 'compose' used herein means to superpose the variation information on the 3-D shape.

The composition results displayed may also include such information as the volumetric change of the person 2 and its waveform, which will be described later.

Here, the output information generation section 24 generates an image as composition information in which the 3-D shape is composed with variation information so that respective measurement points (bright spots) correspond to each other. Incidentally, the analysis information generated is assumed to include determination result produced with the anomaly determination section 26 which will be described later.

The output information generation section 24 is also constituted to carry out the above composition so as to find out the movement of each point on the person 2. Specifically, the variation information, that is, the phase of movement recognized at each measurement point, is superposed on the 3-D shape so that each coordinate corresponds to it. In this way, it is easy to find out for example which point on the body of the person 2 is moving upward or downward.

Referring to FIG. 10, a schematic view, an example of composing a 3-D shape and variation information, in other words an example of generated analysis information, is described. For the description here, the example of generated analysis information is shown as an image displayed on the display 40. As shown in the figure, the 3-D shape described with FIG. 9 and variation information are composed so that respective positions are correlated. When composing the 3-D shape with variation information in this way, phase of movement at each measurement point is made to be recognizable.

Incidentally, FIG. 10(a) shows a case in which the abdomen of the person 2 is moving upward, more specifically inhaling in abdominal breathing. FIG. 10(b) shows a case in which the thorax of the person 2 is moving downward, more specifically exhaling in thorax breathing.

Further in this case, measurement points for the phase of movement are shown in different rendering according to whether the phase of movement is upward or downward (in the figure, upward moving points are shown with blank dots, and downward moving points with solid dots). Different rendering may be made by changing the color of dots (such as blue for upward movement and red for downward). Further, the phases of movement may be indicated with arrows (as shown in the figure with broken lines at some measurement points). In this way, which point of the body of the person 2 is moving upward or downward can be easily recognized. The monitoring apparatus 1 displays the analysis information generated as described above on the display 40. Also in this case, the change in movement can be rendered more easily understandable by changing the depth of color, the breadth of the pattern, the thickness or length of the arrow line, according to the magnitude of change in the waveform movement. Further, also in the case of height change data obtained by integrating the movement change, the height change can be rendered likewise more easily understandable for example by changing the color to a brighter one or increasing the length of arrows in proportion to the increase in height for the points that have moved up.

The output information generation section 24 is also constituted to calculate the volumetric change amount of the person 2. The volumetric change amount can be calculated from the height change amount as the variation information. In this case, for example the sum total of the height change amounts may be assumed to be the volumetric change amount. Calculating the volumetric change amount in this way makes it possible to find out for example the inhalation amount when the person 2 is breathing. The calculated volumetric change amount is made to be included in the analysis information and displayed on the display 40. In case no display is made on the display 40, it may be arranged to store the information in an electronic medium (here, the storage section 31) or the like.

As for the volumetric change amount, in case the volumetric change is occurring periodically, it is possible to obtain the sum total of movement for one cycle by integrating the absolute values over one period (Since data acquisition is carried out at constant intervals, actually by summing up the data). In case of breath detection, half of it corresponds to the tidal volume. In case data are summed up for a period or half a period, it is preferable to determine the start point and the end point of the period as follows: A moving average for several times of volumetric change amounts obtained is calculated. A time point at which the value changes from negative to positive or from positive to negative is assumed to be the start point or the end point. In this way, errors in timing of start and end points are prevented from timing shift of transition between positive and negative values caused by noise contained in the volumetric change amount values.

The output information generation section 24 is also constituted to correct the variation information according to the external shape information, the 3-D shape in this case. To be corrected here is the height change amount as the variation information.

Referring to FIG. 4 again, the correction is described. As seen from the equation (3) described with FIG. 8, the distance h between the imaging lens 13a and the flat surface 102 is required to calculate the height of the object. Likewise, also in case the height change amount is calculated, an appropriate distance h is set and used to calculate the height change amount from the equation (3). While this poses little problem in almost all cases, in case more detailed measurement is to be made, the accurate distance to the point the bright spot is projected to must be known. That is, the distance h between the imaging lens 13a and the solid 103 must be known at each measurement point.

Therefore, the output information generation section 24 corrects the height change amount using the 3-D shape obtained with the 3-D shape generation section 22. Specifically, assuming the height to be h' of the person 2 at each point forming the 3-D shape, the height change amount corresponding to each point is corrected.

A more specific example is described. For example, it is assumed that: the base length of the second FG sensor 10b is 600 mm, the focal distance of the imaging lens 13a of the second image capturing apparatus 12b is 12 mm, and the distance h between the imaging lens 13a and the flat surface 102 is 2.3 m. If a bright spot on the image plane 15' shifts 5 micrometers, a height change amount is calculated to be 3.67 mm. If the distance between the imaging lens 13a and the solid 103 is assumed to be 2.0 m (or the height of the solid 103 is 0.3 m) and this is used as h, the height change amount is calculated to be 2.77 mm. The difference of 1.1 mm in height change amount is the measurement error.

As described above, since the output information generation section 24 can calculate the height change amount by the above correction using the accurate distance h, it is possible to find out more accurate height change amount. Further it is possible to measure the volumetric change of the person 2 more accurately by calculating the volumetric change according to the height change amount corrected as described above. This is very effective in measuring the amount of slight movement such as breathing.

Referring again to FIG. 3, a movement discrimination section 25 is provided in the control section 21 for determining the kind of movement of the person 2 based on the movement information measured with the measurement device 14 of the second FG sensor 10b. That is, the movement discrimination section 25 discriminates the kind of movement of the person 2 based on the movement information, that is, the movement in the height direction of the person 2, measured at a plurality of measurement points with the measurement device 14. The kinds of movement of the person 2 to be determined with the movement discrimination section 25 are typically: breathing, bodily motion, and immobility (without motion). The movement discrimination section 25 is further constituted to detect the breathing of the person 2 based on the movement information. The bodily motion is that of the person 2, a concept broadly including for example the motion of arms and legs as well as standing up and sitting.

It is preferable to constitute the movement discrimination section 25 to detect breathing of the person 2 in case the breathing is recognized. The breath detection with the movement discrimination section 25 may be arranged to detect the breath by determining whether or not a movement is a breath by setting upper and lower threshold values to one or both of amplitude and period (frequency) of periodic change with time in the above average value and determining whether or not it is a breath by comparing with the threshold values. The upper and lower threshold values of period may be set to a range including for example the period of human breath, such as 5 cycles per minute for the lower threshold and 60 cycles per minute for the upper threshold. Incidentally, while the number of breaths is in the range of about 5 to 30 per minute for adults, that for infants tends to be greater. The detected breath of the person 2 forms a waveform pattern.

FIG. 11 shows an example of the breath waveform pattern.

Further the movement discrimination section 25 is preferably made to detect the number of breaths. The number of breaths may be detected for example by performing data processing such as Fourier conversion of the change with time in the sum total of the bright spot shift amount in the area where the movement is determined to be that of breathing.

In the control section 21 is further provided an anomaly determination section 26 for determining the anomaly of the person 2 based on the movement in the height direction of the person 2 measured with the measurement device 14 of the second FG sensor 10b. To put it more specifically, the anomaly determination section 26 determines anomaly of the person 2 based on the results of breath of the person 2 detected with the movement discrimination section 25. Further, the anomaly determination section 26 is also anomaly determination means for determining the anomaly of the person 2 based on the variation information obtained with the variation information computing section 23. Determining the anomaly of the person 2 in this case means determining whether or not the person 2 is in a critical condition.

The determination criteria for the critical state of the person 2 with the anomaly determination section 26 may be set in consideration of the following. For example, in case the period characteristic of the breathing pattern shows disorder within a short period of time or changes abruptly while breathing is being detected with the movement discrimination section 25, occurrence of disorder is suspected such as: lung diseases such as spontaneous pneumothorax and bronchial asthma; heart diseases such as congestive heart failure; and cerebrovascular diseases such as cerebral hemorrhage. Therefore, setting should be made to determine the above state to be critical. In case disappearance of breathing pattern lingers, a stop of breathing of the person 2 is suspected. Therefore, setting should be made to determine the state to be critical. In case bodily movement rather than the breath pattern appears frequently within a short period of time, a situation is suspected in which the person 2 is thrashing in agony due to some causes. Therefore, setting should be made to determine the state to be critical.

The above determination results with the anomaly determination section 26 is made to be displayed on the display 40. The anomaly determination section 26 outputs the determination results to the output information generation section 24. In this case, the output information generation section 24 generates and outputs analysis information including the determination results to the display 40. In this way, as the determination results produced with the anomaly determination section 26 are displayed on the display 40, for example a measurement operator can easily recognize anomaly of the person 2.

While the above description is made assuming that the pattern projected on the bed 3 is made up of a plurality of bright spots, the pattern may be made up of bright lines as shown in FIG. 12. That is, the movement in the height direction of the person 2 may be measured using the optical tomography. In this case, a projecting device 111 is used that is constituted to project a light pattern of bright lines on the bed 3. While the number of bright lines to be projected is typically plural, it may be singular. In case of a single bright line, a method of scanning with the single bright line may be used. The following is the explanation of using a plurality of bright lines. The bright lines 111b are projected at equal intervals.

The bright lines 111b form a pattern 111a'. The direction of the bright lines 111b is approximately vertical to the base line of triangulation.

When the bright lines are used as shown in FIG. 13, like when using the bright spots explained with FIG. 5, due to the presence of a solid of a height, the image of a bright line imaged on the image plane 15' of the image sensor 15 shifts by an amount of δ in the direction of y-axis. Further likewise, positions on the solid can be specified in three dimensions by the measurement of the δ. The measurement of the δ is carried out on the centerline of the image of the bright line. When the bright lines are used, the measurement point corresponds to one pixel of the image sensor 15 located on the image of the bright line.

As described above, using the light pattern of a plurality of bright lines and measuring the shift of the bright lines make it possible, unlike using the light pattern of a plurality of bright spots, to measure the movement of any point on the bright line, so that continuous shape along the bright line direction can be recognized. In other words, measurement resolution in the direction of bright line is improved.

While the person 2 is used as an object in the above explanation, the object may be a machine such as an electric motor. In that case, it is possible to measure relatively slight movement, the vibration, of the motor.

Further in the above explanation, the first 3-D sensor and the second 3-D sensor use a common projecting device. However, the arrangement is not limited to the above but may use a common image capturing apparatus serving as both the first and second image capturing apparatus s, and use two projecting devices. In other words, in FIG. 1 as described above, in the first FG sensor 10a and the second FG sensor 10b, the projecting device 11 is common. However, it may be arranged as shown in FIG. 14 that the first FG sensor 10a has a first projecting device 11-1, the second FG sensor 10b has a second projecting device 11-2, and the first and second image capturing apparatus 12a and 12b are replaced with a common image capturing apparatus 12.

In that case, the first FG sensor 10a and the second FG sensor 10b are placed so that the first projecting device 11-1 and the image capturing apparatus 12 are located about above the center of the bed 3, and the second projecting device 11-2 is located about above the head of the person 2. The first projecting device 11-1 is placed at an interval of d1 from the image capturing apparatus 12, and the second projecting device 11-2, at a second interval of d2.

Further in this case, the projected patterns are not common. To wit, since the pattern 11a is projected from the first projecting device 11-1 and the pattern 11a' from the second projecting device 11-2, the process of composing the 3-D shape and the variation information with the output information generation section 24 is slightly different. Specifically, composition using the output information generation section 24 is made to put together the 3-D shape and the variation information so that coordinates on the bed 3 correspond rather than that measurement points of FG sensors 10 correspond to each other. In this way, the 3-D shape and the variation information are put together accurately even if there are differences in the position of projected pattern and in the pitch of the bright spots between FG sensors 10.

Further in this case, when capturing an image of the pattern with the image capturing apparatus 12, it is necessary to discriminate which of the first projecting device 11-1 and the second projecting device 11-2 has projected the pattern. To do so for example, it may be arranged that both the projecting devices do not project patterns simultaneously. The image captured when the pattern 11a is projected with the first projecting device 11-1 and the image captured when the pattern 11a' is projected with the second projecting device 11-2 should be processed separately. In this way, it is possible to measure the shifts of the pattern 11a and the pattern 11a', and obtain the 3-D shape and the variation information.

As described above, in case the single image capturing apparatus serves as both the first and second image capturing apparatus, and two projecting devices are used, the common use of the single image capturing apparatus reduces for example the amount of image processing.

As described above, since the monitoring apparatus 1 is provided with: the first FG sensor 10a, the second FG sensor 10b, the 3-D shape generation section 22, and the variation information computing section 23, it is possible to obtain the 3-D shape of the person 2, based on the height information obtained with the first FG sensor 10a, using the 3-D shape generation section 22, and to obtain the variation information on the person 2, based on the movement information obtained with the second FG sensor 10b, using the variation information computing section 23. Further, providing the output information generation section 24 for putting together the 3-D shape and the variation information makes it possible to produce a image that makes it easy to recognize, for example, which point on the body of the person 2 is moving upward or downward. This enables easy and accurate recognition of the state, in particular breathing state, of the person 2.

Since the first FG sensor 10a has a relatively short placement interval (baseline length) between the projecting device and the image capturing apparatus, the leap of the bright spot described before is less likely to occur, so that it is suitable for measuring, for example, the external shape of the person 2. Further, since the second FG sensor 10b has a longer placement interval between the projecting device and the image capturing apparatus (baseline length) in comparison with the first FG sensor 10a, it is possible to accurately measure even a slight movement such as breathing of the person 2.

Further, since the 3-D shape generation section 22 generates the 3-D shape that enables recognition of the physical shape of the person 2, the state of breathing of the person 2 is easy to grasp. Using the FG sensor 10 as the 3-D sensor, while being simple, makes it possible to accurately measure the movement in the height direction of the person 2. Moreover, since the FG sensor 10 can make measurements without contact, the person being measured is less stressed.

Since the output information generation section 24 corrects the variation information according to the 3-D shape, the height change amount of the person 2 is more accurately calculated. Since the volumetric change amount is calculated according to the height change amount, the volumetric change amount is more accurately calculated.

The monitoring apparatus 1 is provided with the display 40 for displaying the composed results of the output information generation section 24. Thus, the monitoring apparatus 1 can display on the display 40 the results composed with the output information generation section 24, the analysis information produced by superposing the variation information representing the bodily movement of the person 2 on the 3-D shape, the external body shape of the person 2. Therefore, the movement of every point on the human body (in particular breathing movement) can be easily recognized. This can be useful as a reference for diagnosis by doctors.

Moreover, since the 3-D shape generation section 22 makes interpolation for missing points on the 3-D shape, continuous external shape of the person 2 is obtained even when measurement points are located at great intervals.

BRIEF DESCRIPTION OF DRAWINGS

FIG. 10(a) is a schematic view when the abdomen makes an upward movement, and FIG. 10(b) is a schematic view when the thorax makes a downward movement.

DESCRIPTION OF REFERENCE NUMERALS AND SYMBOLS

Figure 1:
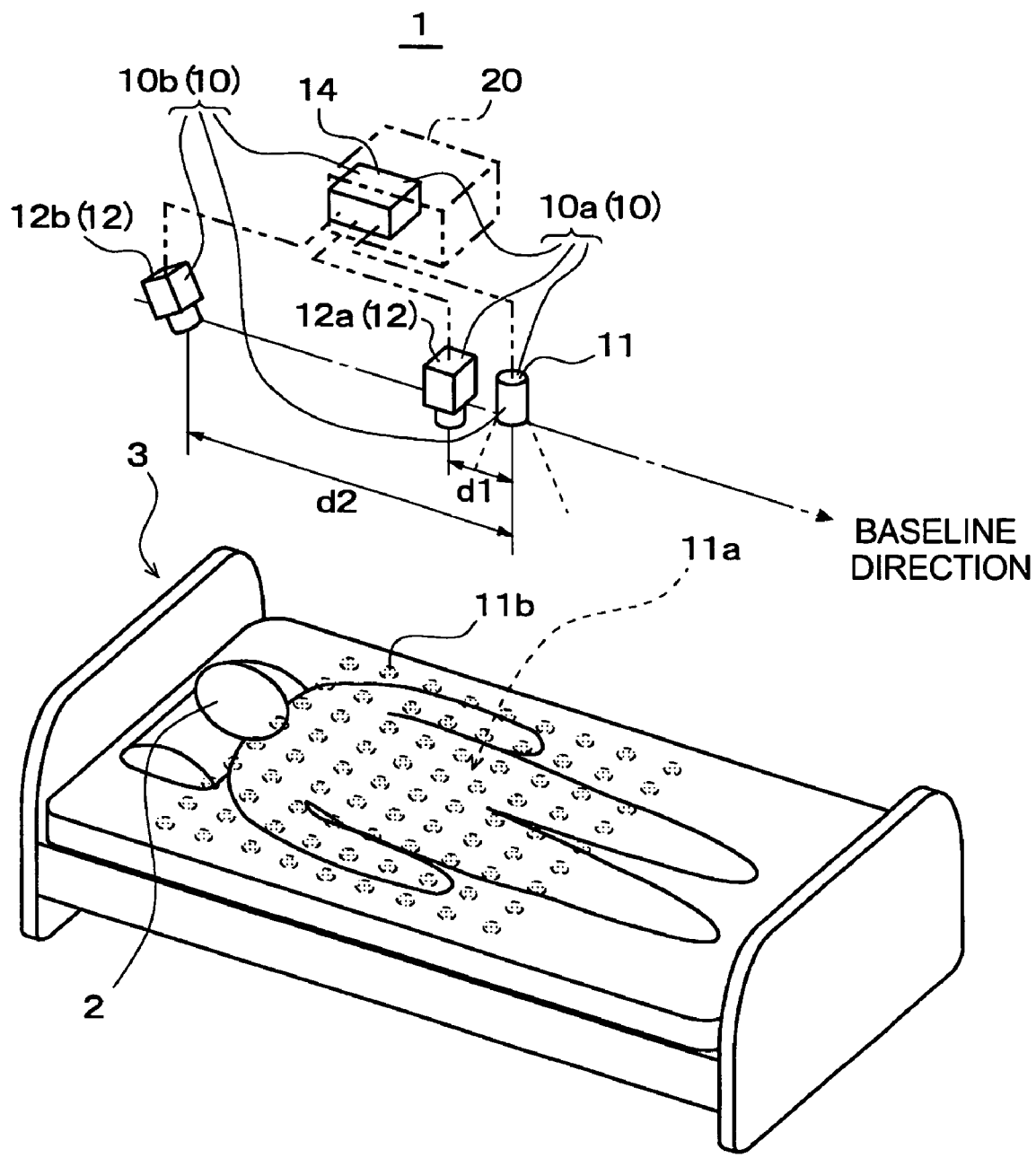
FIG. 1 is a schematic external view, roughly showing a monitoring apparatus of an embodiment according to the invention.
Figure 2:
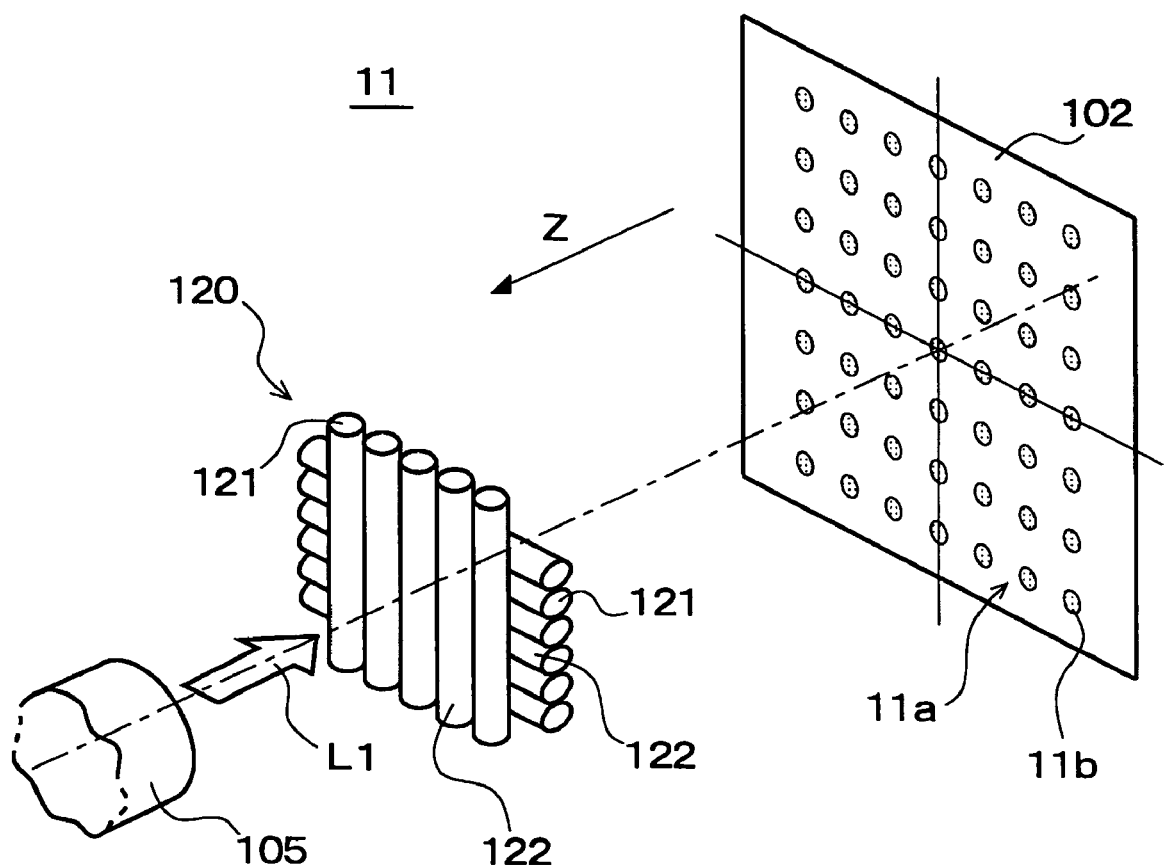
FIG. 2 is a schematic perspective view, illustrating a projecting device of an embodiment according to the invention.
Figure 3:
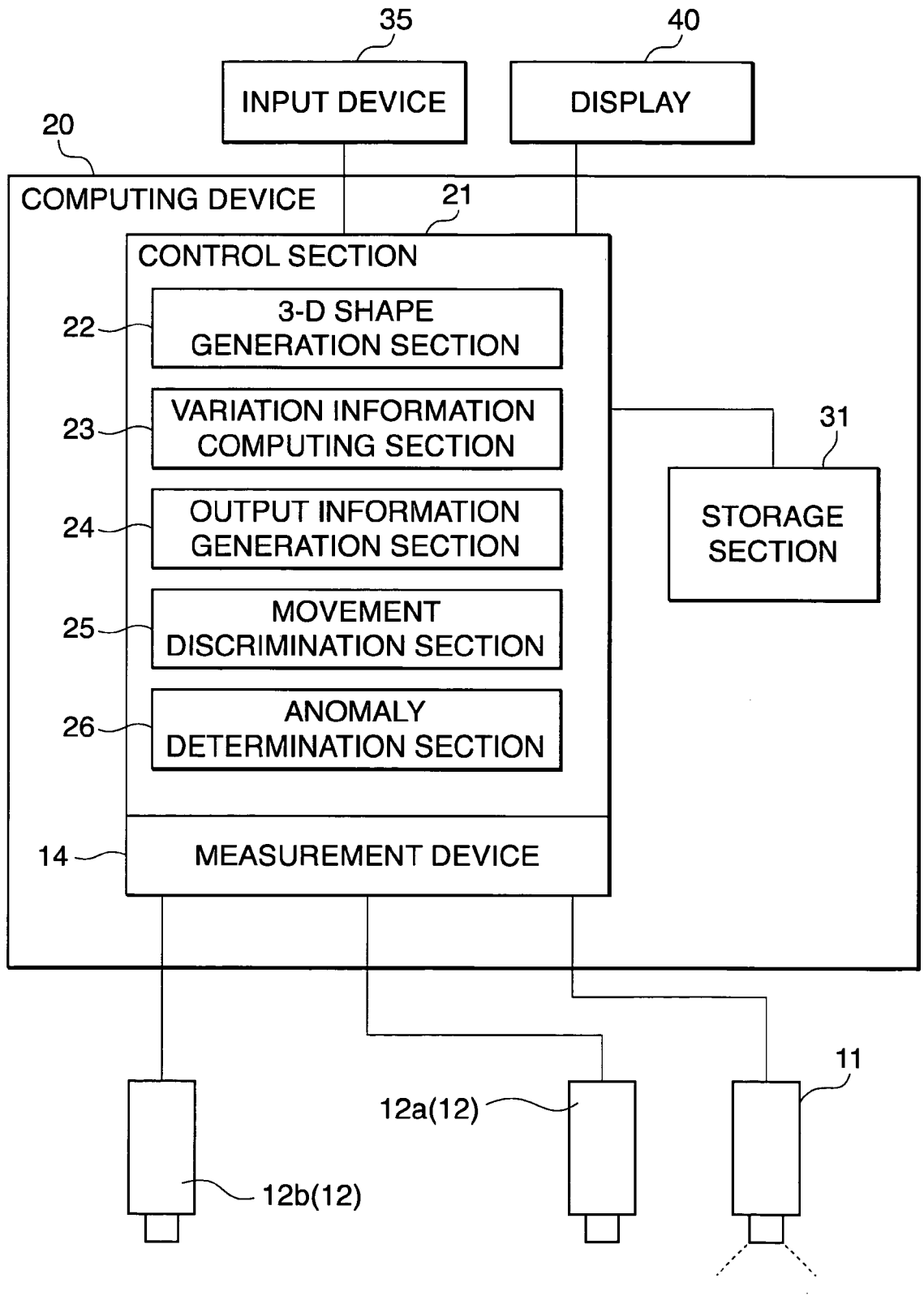
FIG. 3 is a block diagram, showing an exemplary constitution of a monitoring apparatus of an embodiment according to the invention.
Figure 4:
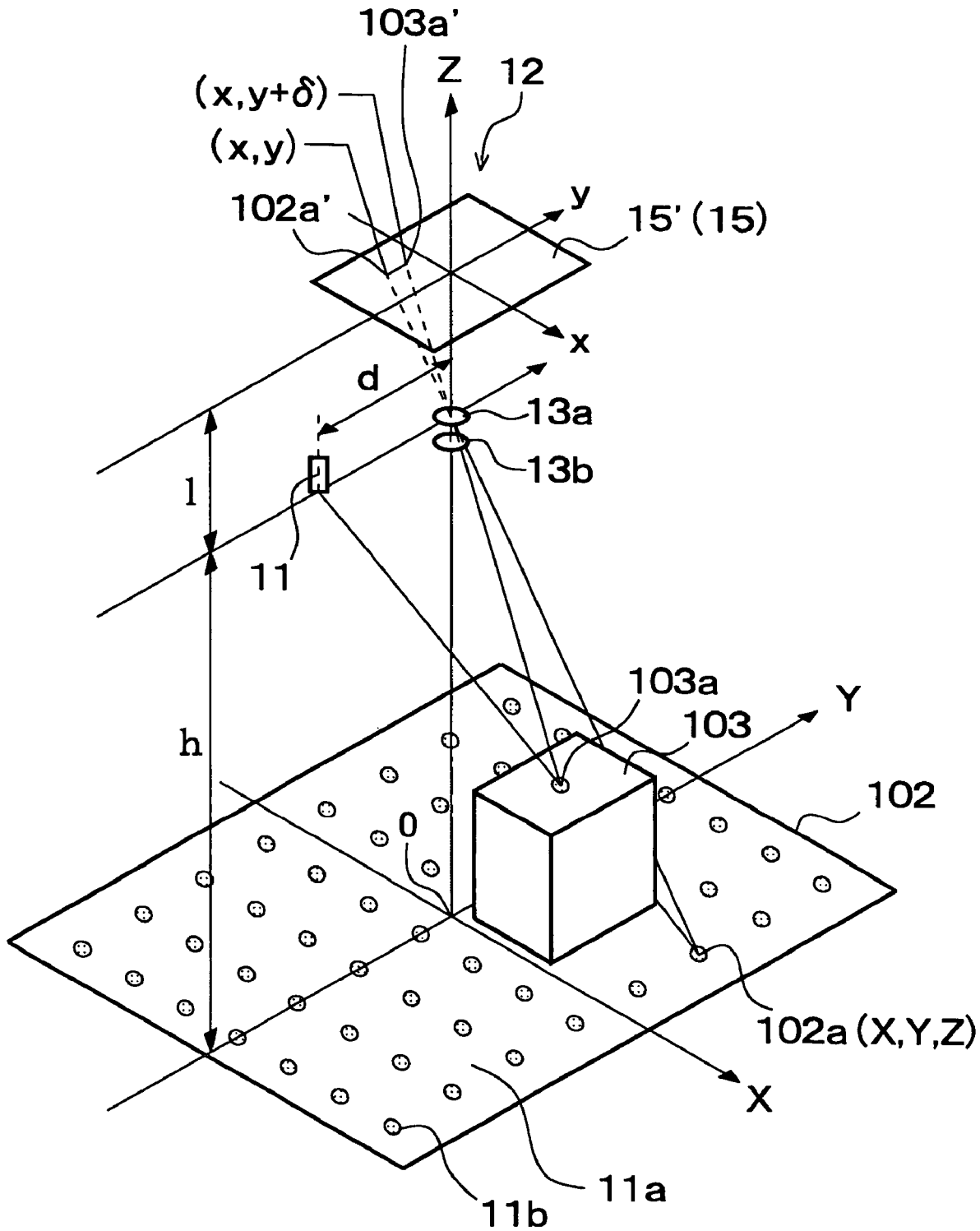
FIG. 4 is a conceptual perspective view for explaining the concept of bright spot shift in an embodiment according to the invention.
Figure 5:
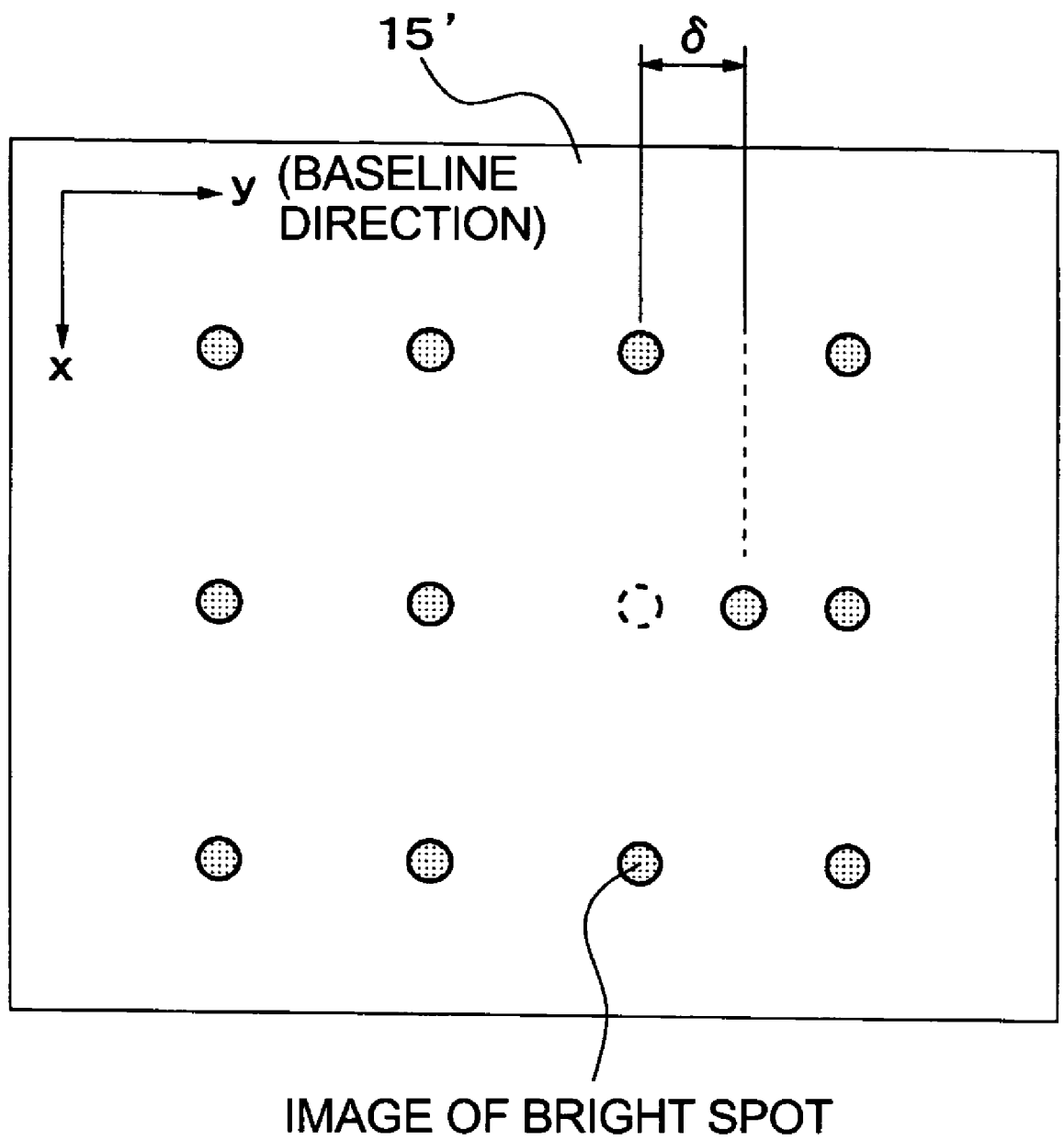
FIG. 5 is a schematic view for explaining the bright spot imaged on an image plane in the case of FIG. 4.
Figure 6:
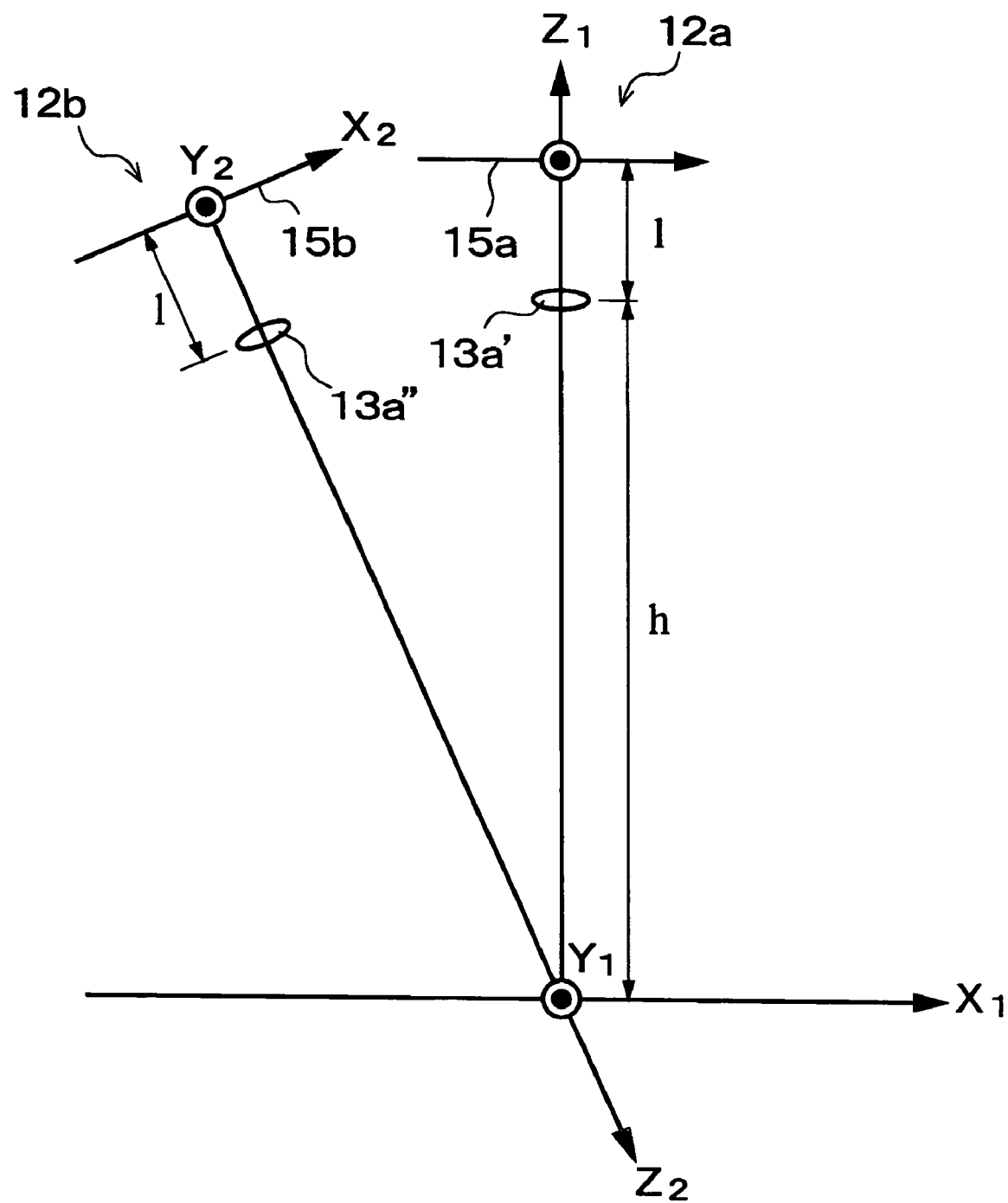
FIG. 6 is a line drawing for explaining conversion of coordinates when the bright spots are correlated between the first and second image capturing apparatus in an embodiment according to the invention.
Figure 7:
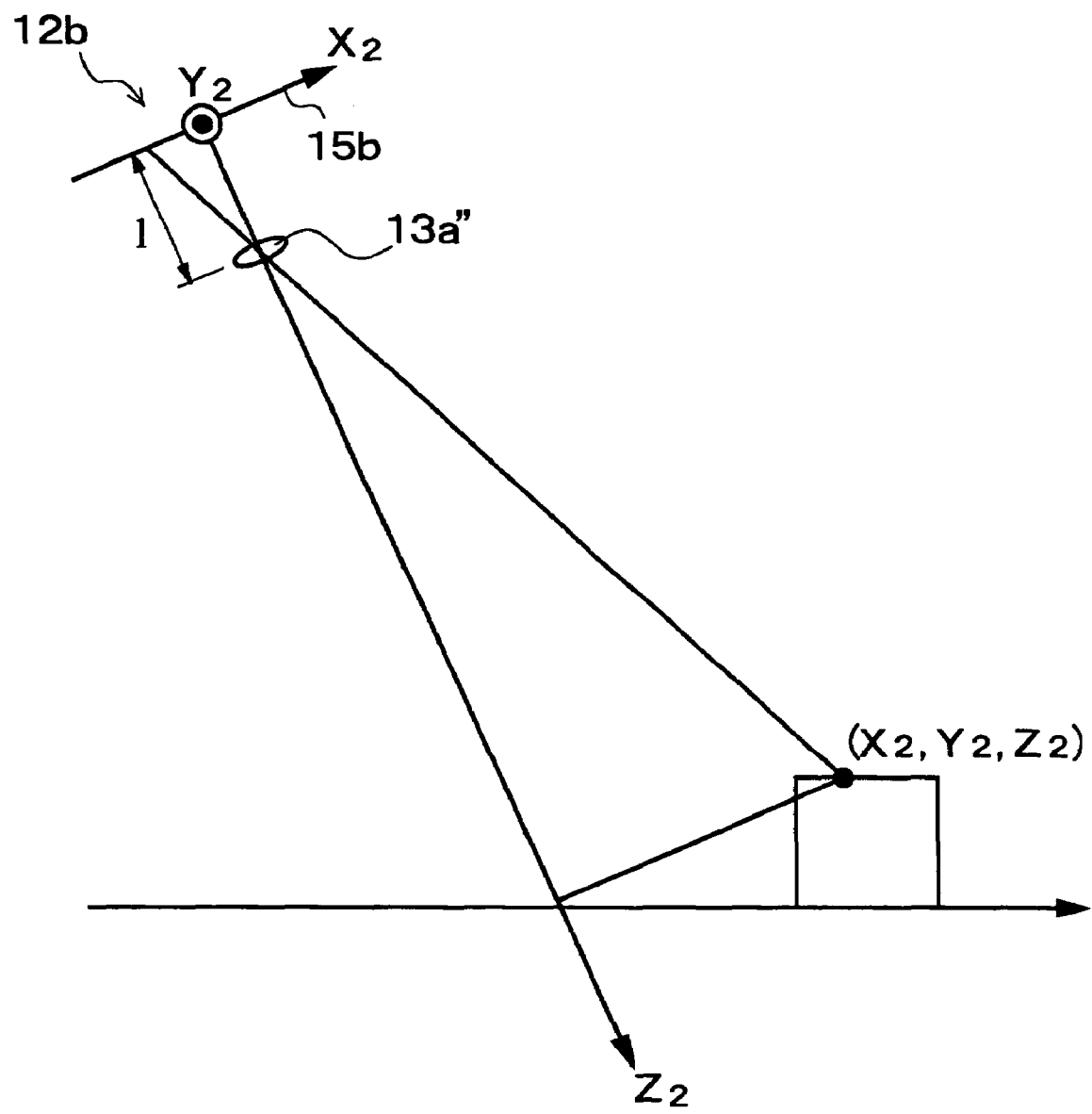
FIG. 7 is a line drawing for explaining about utilizing similarity in the case of FIG. 6.
Figure 8:
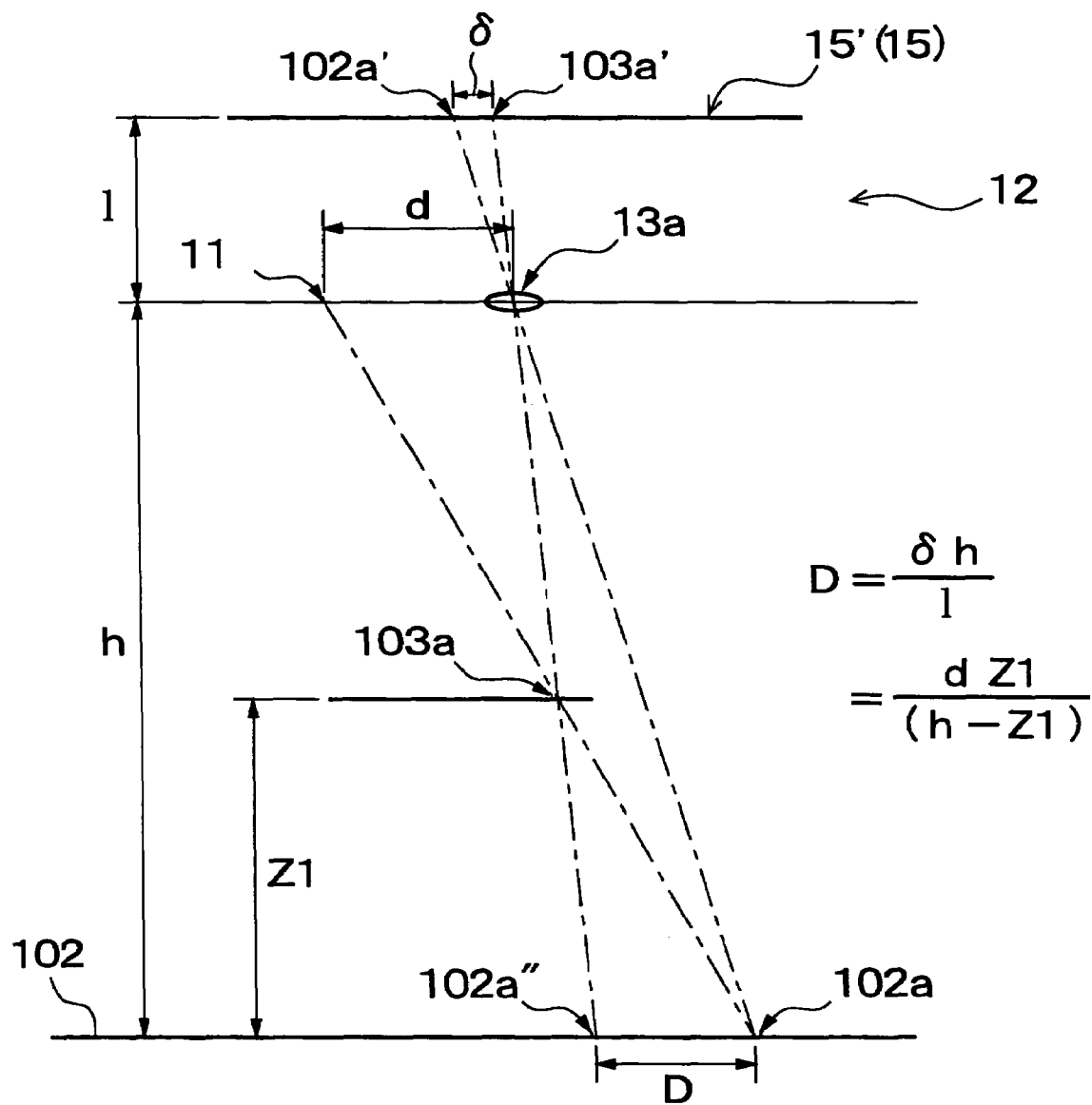
FIG. 8 is a line drawing for explaining about calculating the height of object in an embodiment according to the invention.
Figure 9:
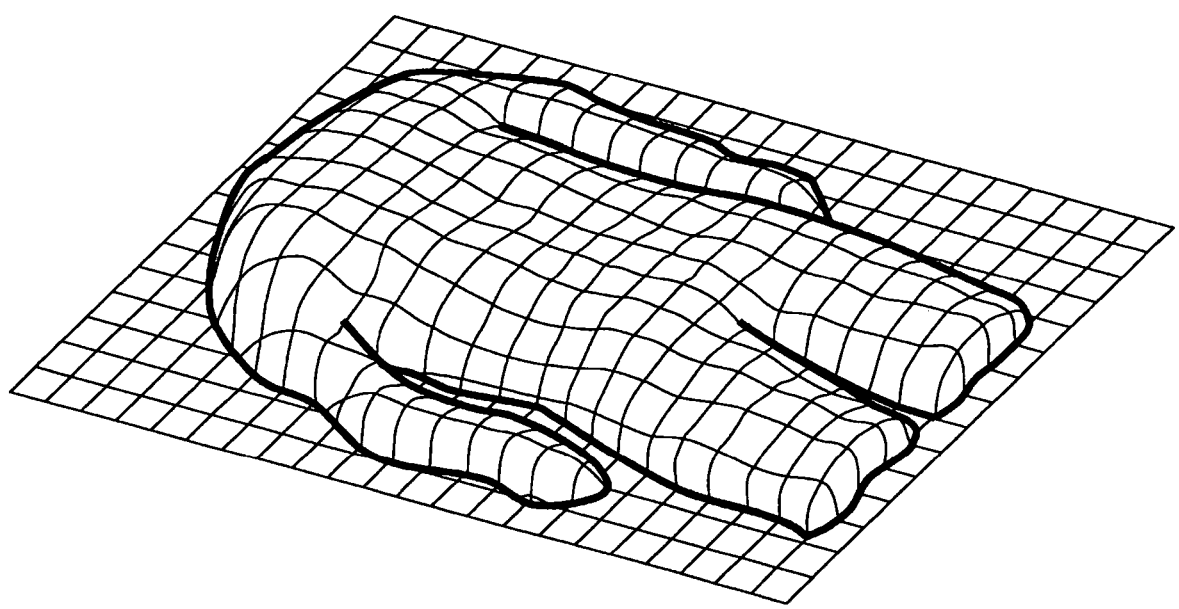
FIG. 9 is a schematic view for explaining the 3-D shape generated with a 3-D shape generation section of an embodiment according to the invention.
Figure 10:
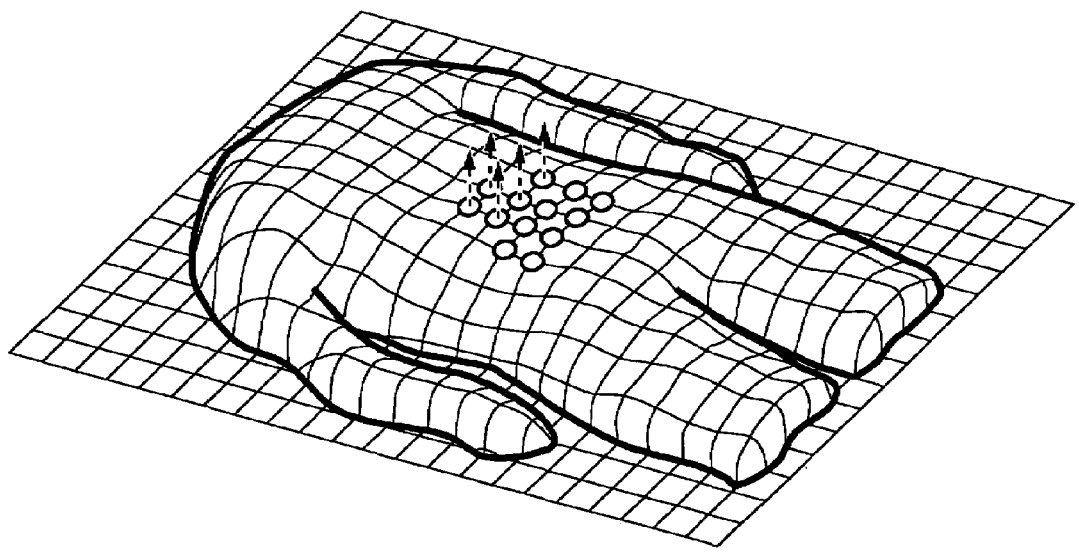
FIG. 10 is a schematic view showing exemplary results obtained by composing the 3-D shape with the variation information in the case of FIG. 9.
Figure 10:
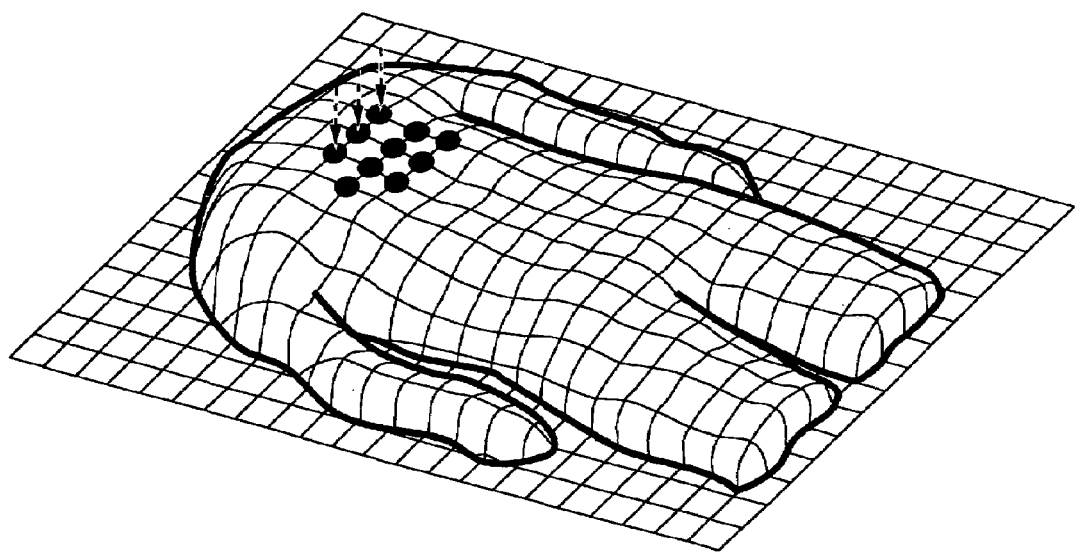
Figure 11:
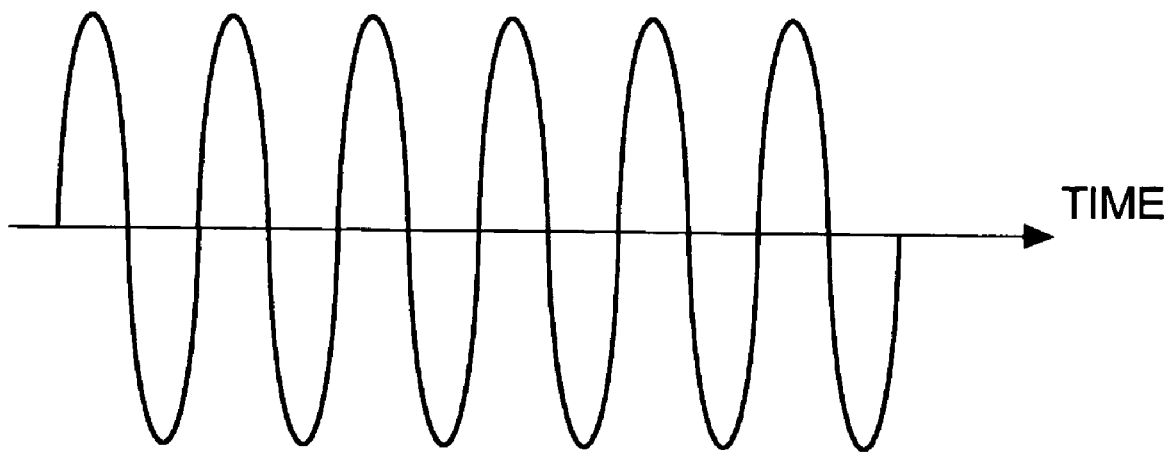
FIG. 11 is a line drawing, showing a breath waveform pattern used in an embodiment of the invention.
Figure 12:
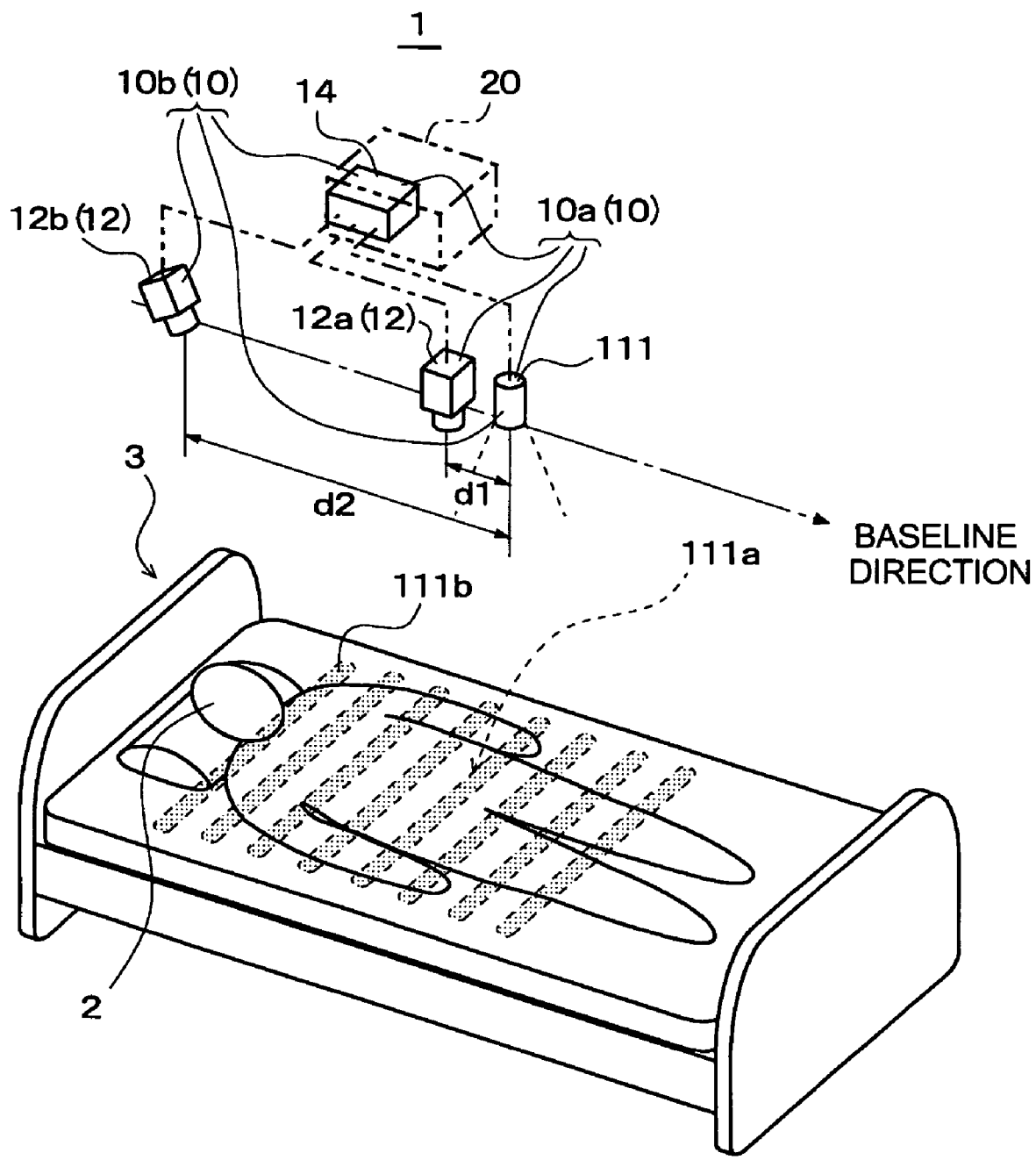
FIG. 12 is a schematic external view of a monitoring apparatus in case a plurality of bright lines are used to make up a light pattern projected from a projecting device of an embodiment according to the invention.
Figure 13:
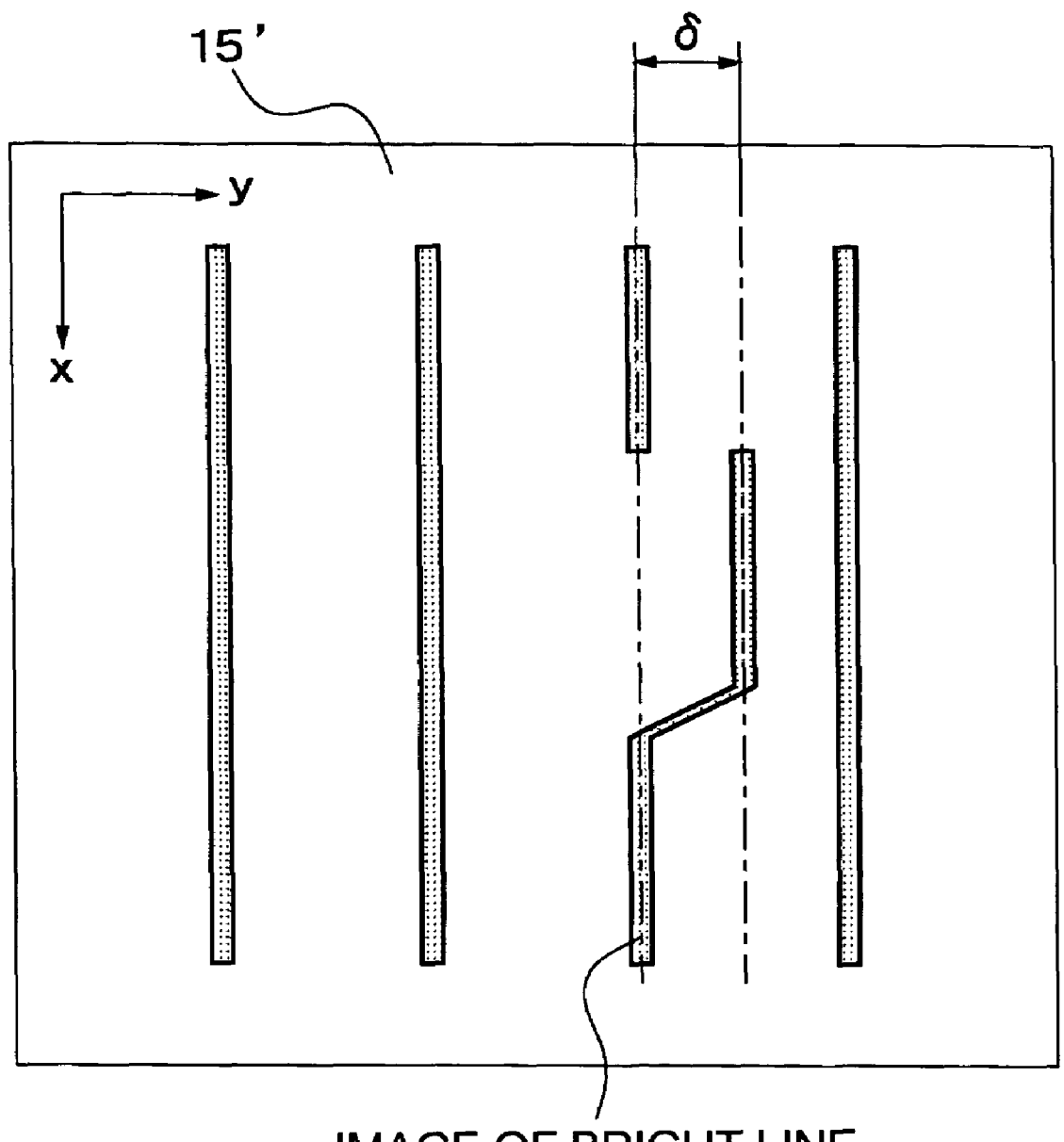
FIG. 13 is a schematic view for explaining bright lines imaged on an image plane in the case of FIG. 12.
Figure 14:
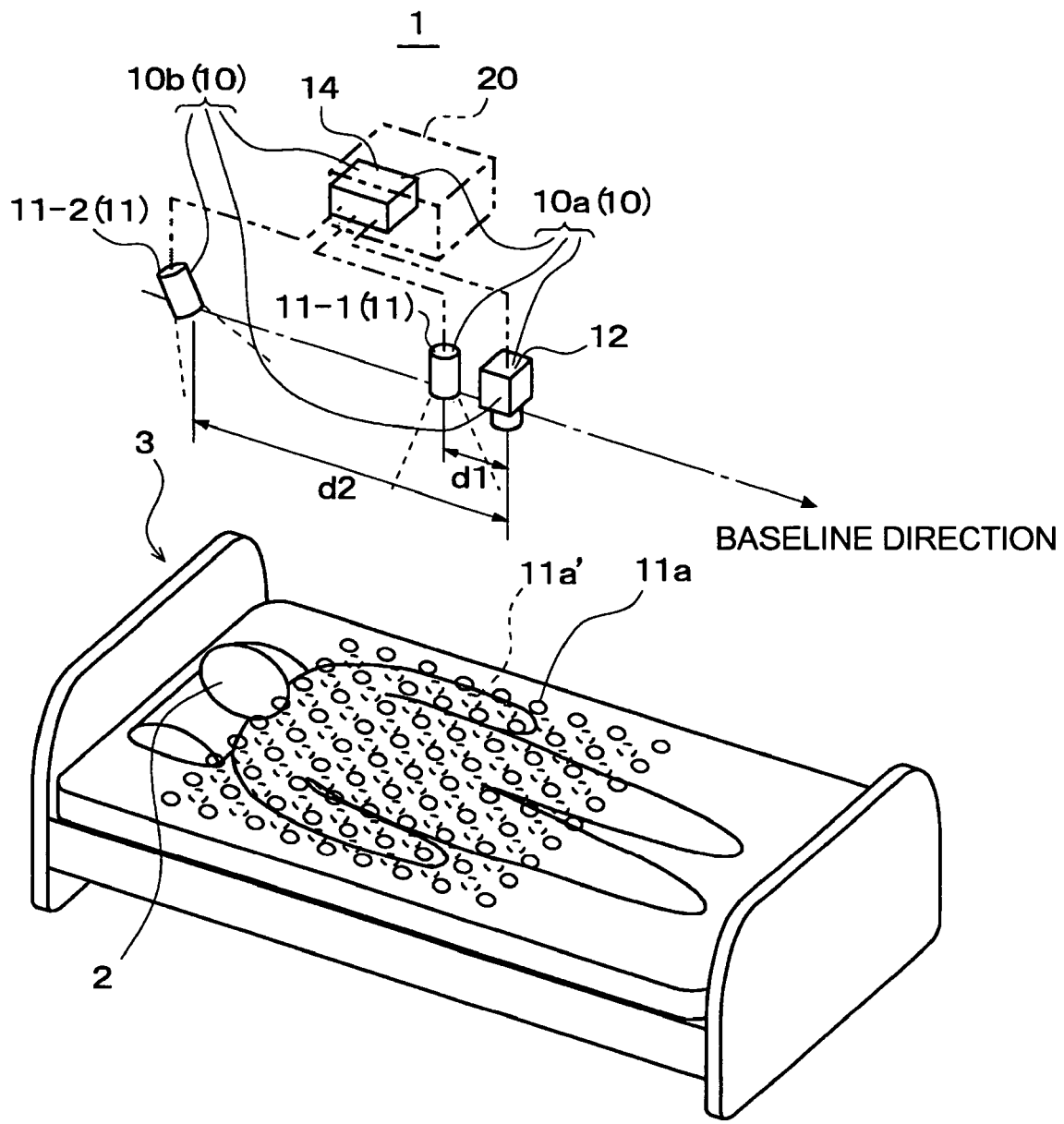
FIG. 14 is a schematic external view of a monitoring apparatus provided with a image capturing apparatus for common use as both the first and second image capturing apparatus, and with two projecting devices, in an embodiment of the invention.

1: monitoring apparatus
2: person
3: bed
10: FG sensor
10a: first FG sensor
10b: second FG sensor
11: projecting device
11a: pattern
11b: bright spot
12: image capturing apparatus
12a: first image capturing apparatus
12b: second image capturing apparatus
14: measurement device
20: computing device
21: control section
22: 3-D shape generation section
23: variation information computing section
24: output information generation section
25: movement discrimination section
26: anomaly determination section
40: display
102: flat surface
103: solid
105: light beam generation section
120: grating
121: optical fiber
122: FG element

The invention claimed is:

1. A three-dimensional shape measurement apparatus comprising:

a first three-dimensional sensor having a projecting device for projecting a light pattern on a target area, and an image capturing apparatus placed at a first interval from the projecting device to capture an image of the target area on which the light pattern is projected;

a second three-dimensional sensor having a projecting device for projecting a light pattern on the target area, and an image capturing apparatus placed at a second interval longer than the first interval from the projecting device to capture an image of the target area on which the light pattern is projected;

three-dimensional information computing means for obtaining external shape information on an object present in the target area based on a first shift of the pattern on an image acquired with the first three-dimensional sensor, wherein said first shift of the pattern is a shift from a base image captured at a time point at which the object is not present in the target area to a captured image captured at an arbitrary time point at which the object is present in the target area;

variation information computing means for obtaining variation information on the object based on a second shift of the pattern on the image acquired with the second three-dimensional sensor, wherein said second shift of the pattern is a shift from a reference image captured at a first arbitrary time point at which the object is present in the target area to a captured image captured at a second arbitrary time point after the first arbitrary time point with enough time interval for detecting a movement of the object and at which the object is present in the target area; and information composing means for composing the external shape information and the variation information.

2. The three-dimensional shape measurement apparatus as recited in claim 1, wherein the information composing means corrects the variation information based on the external shape information.

3. The three-dimensional shape measurement apparatus as recited in claim 1, wherein the information composing means performs the composition so as to find out the movement of each point of the object.

4. The three-dimensional shape measurement apparatus as recited in claim 2, wherein the information composing means performs the composition so as to find out the movement of each point of the object.

5. The three-dimensional shape measurement apparatus as recited in claim 1, further comprising information output means for displaying the composed results of the information composing means.

6. The three-dimensional shape measurement apparatus as recited in claim 2, further comprising information output means for displaying the composed results of the information composing means.

7. The three-dimensional shape measurement apparatus as recited in claim 3, further comprising information output means for displaying the composed results of the information composing means.

8. The three-dimensional shape measurement apparatus as recited in claim 1, wherein the light pattern is an array of bright spots.

9. The three-dimensional shape measurement apparatus as recited in claim 2, wherein the light pattern is an array of bright spots.

10. The three-dimensional shape measurement apparatus as recited in claim 3, wherein the light pattern is an array of bright spots.

11. The three-dimensional shape measurement apparatus as recited in claim 1, wherein the three-dimensional information computing means performs interpolation for points that lack the external shape information.

12. The three-dimensional shape measurement apparatus as recited in claim 2, wherein the three-dimensional information computing means performs interpolation for points that lack the external shape information.

13. The three-dimensional shape measurement apparatus as recited in claim 3, wherein the three-dimensional information computing means performs interpolation for points that lack the external shape information.

* * * * *